US008278265B2

(12) United States Patent
Yamane et al.

(10) Patent No.: US 8,278,265 B2
(45) Date of Patent: Oct. 2, 2012

(54) METHODS, KITS AND COMPOSITIONS COMPRISING CROTAMINE

(75) Inventors: Tetsuo Yamane, São Paulo SP (BR); Irina Kerkis, São Paulo SP (BR); Alexandre Kerkis, São Paulo SP (BR); Gandhi Rádis Baptista, São Paulo SP (BR); Mirian Akemi Furuie Hayashi, São Paulo SP (BR); Katsuhiro Konno, São Paulo SP (BR); Alvaro Rossan B. P. Da Silva, São Paulo SP (BR); Lygia da Veiga Pereira, São Paulo SP (BR); Eduardo Brandt De Oliveira, Ribeirão Preto SP (BR)

(73) Assignee: Fundacao de Amparo a Pesquisa do Estado de Sao Paulo—FAPESP, Sao Paulo (BR)

( * ) Notice: Subject to any disclaimer, the term of this patent is extended or adjusted under 35 U.S.C. 154(b) by 206 days.

(21) Appl. No.: 11/902,064

(22) Filed: Sep. 18, 2007

(65) Prior Publication Data

US 2008/0181849 A1 Jul. 31, 2008

Related U.S. Application Data

(63) Continuation of application No. PCT/BR2006/000052, filed on Mar. 17, 2006.

(30) Foreign Application Priority Data

Mar. 18, 2005 (BR) ..................................... 0501037

(51) Int. Cl.
*A61K 49/00* (2006.01)
*C12Q 1/02* (2006.01)

(52) U.S. Cl. .......... 514/1.2; 530/856; 435/375; 424/542

(58) Field of Classification Search ........................ None
See application file for complete search history.

(56) References Cited

U.S. PATENT DOCUMENTS

| | | | | | |
|---|---|---|---|---|---|
| 4,731,439 | A | * | 3/1988 | Marquardt et al. | 530/324 |
| 4,774,318 | A | * | 9/1988 | Marquardt et al. | 530/324 |
| 5,053,492 | A | * | 10/1991 | Rael et al. | 530/391.1 |

(Continued)

OTHER PUBLICATIONS

Kerkis, Alexandre et al, The FASEB Journal, Published online Jul. 1, 2004, pp. 1-20, express article 10.1096/fj.03-1459fje.*

(Continued)

*Primary Examiner* — Albert Navarro
*Assistant Examiner* — Ginny Portner
(74) *Attorney, Agent, or Firm* — Arent Fox LLP

(57) ABSTRACT

The present invention refers to uses of crotamine and compositions containing it, based on its characteristic of interaction with genetic material. Under submicromolar quantities, the polypeptide is no longer toxic, presenting the characteristics properties of cell penetration, transport of molecules to the surface, cytoplasm or cell nucleus and particularly, selective cell penetration.

The invention also refers to compositions comprising a pharmaceutically effective concentration of crotamine and its use for the treatment of diseases and dysfunctions, based on its characteristics of interaction with genetic material, such as DNA and RNA, and cell selectivity.

Further, the invention refers to a kit comprising crotamine as a reagent to: (i) transfect or carry molecules to the surface, cytoplasm or nucleus of the cell or (ii) identify and select actively proliferating cells in a homogeneous and/or mixed cell population, particularly the ones originated from the umbilical cord and/or bone marrow and others undifferentiated cells such as progenitors and stem cells from different sources of organism and cancer cells.

8 Claims, 10 Drawing Sheets

U.S. PATENT DOCUMENTS

| | | | | |
|---|---|---|---|---|
| 5,164,196 | A * | 11/1992 | Plata et al. | 424/542 |
| 5,232,911 | A * | 8/1993 | Vidal | 514/12 |
| 5,989,857 | A * | 11/1999 | Mundschenk | 435/69.1 |
| 6,420,176 | B1 | 7/2002 | Lisziewicz et al. | |
| 6,461,641 | B1 | 10/2002 | Fick | |
| 6,635,623 | B1 | 10/2003 | Hoogeveen et al. | |
| 6,638,767 | B2 | 10/2003 | Unger et al. | |
| 6,670,148 | B2 * | 12/2003 | Mundschenk et al. | 435/69.1 |
| 6,676,935 | B2 | 1/2004 | Henderson et al. | |
| 6,680,301 | B2 | 1/2004 | Berg et al. | |
| 6,692,911 | B2 | 2/2004 | Pack et al. | |
| 7,094,575 | B2 * | 8/2006 | Gopalakrishnakone et al. | 435/69.2 |
| 7,422,890 | B2 * | 9/2008 | Gopalakrishnakone et al. | 435/252.3 |
| 2003/0027764 | A1 * | 2/2003 | Gopalakrishnakone et al. | 514/12 |
| 2003/0215437 | A1 * | 11/2003 | Mundschenk et al. | 424/94.63 |
| 2006/0045875 | A1 * | 3/2006 | Reid | 424/94.63 |
| 2006/0078551 | A1 * | 4/2006 | Gopalakrishnakone et al. | 424/94.2 |
| 2006/0234299 | A1 * | 10/2006 | Stemmer et al. | 435/7.1 |
| 2007/0014735 | A1 * | 1/2007 | Mundschenk | 424/45 |
| 2007/0128179 | A1 * | 6/2007 | Gopalakrishnakone et al. | 424/94.6 |
| 2007/0148159 | A1 * | 6/2007 | Reid et al. | 424/94.64 |

OTHER PUBLICATIONS

Hayashi, Mirian A.F. et al, Toxicon, vol. 52(2008), pp. 508-517, Cytotoxic effects of crotamine are mediated through lysosomal membrane permeabilization.*

Griffin, Patrick R et al, FEBS letters, Nov. 1990, vol. 274(1-2), pp. 43-47, A new small myotoxin from the venom of prairie rattlesnake (*Crotalus viridis viridis*).*

Rados-Baptista et al, Toxicon, vol. 37, pp. 979-984, 1999, Nucleotide sequence of crotamine isoform precursors from a single South American rattlesnake (*Crotalus durissus terrificus*).*

Schweitz, Hugues et al, Biochemistry, 1981, vol. 20, pp. 5245-5252, Purification and Pharmacological Properties of Eight Sea Anemone toxins from *Anemonia sulcata, Anthopleura xanthogrammica*, Stoichactis giganteus and Antinodendron plumosum.*

Chang, CC et al, British Journal of Pharmacology, 1983, vol. 79, pp. 673-680, A study on the membrane depolarization of skeletal muscles caused by a scorpion toxin, sea anemone toxin II and crotamine and the interaction between toxins.*

Cura, JE et al, Clinical Cancer Research, vol. 8, pp. 1033-1041, Apr. 2002, Phase I and Pharmacokinetics Study of Crotoxin (Cytoxic PLA2 NSC-624244) in Patients with Advanced Cancer.*

Fouda, Fatma M (Egyptian Journal of Biology, 2005, vol. 7, pp. 1-13, Anti-tumor Activity of tetrodotoxin extracted from the Masked Puffer Fish *Arothron diadematus*.*

Boni-Mitake, et al, Toxicon, vol. 48, pp. 550-555, 2006, Distribution of 125-I-labeled crotamine in mice tissues.*

Journal of Venomous Animal and Toxins, vol. 6, (2), Botucatu, 2000, abstract, Biochemical and pharmacological studies of native and irradiated crotamine with gamma radiation of Co60.*

Baker, B et al, Toxicon, Mar. 1993, vol. 31(3), pp. 271-284, Binding of myotoxin a to cultured muscle cells.*

Chang, C.C. et al, British Journal of Pharmacology, 1978, vol. 63, pp. 551-559, Effe4ct of crotamine, a toxin of South American Rattlesnake venom on the sodium channel of murine skeletal muscle.*

N.C. Talbot et al, "Alkaline Phosphatase Staining of Pig and Sheep Epiblast Cells in Culture", *Molecular Reproduction and Development*, 1993, 36, pp. 139-147.

J. Hawiger, "Noninvasive Intracellular Delivery of Functional Peptides and Proteins", pp. 89-94.

S.J. Hong et al, "Electrophysiological Studies of Myotoxin *a*, Isolated from Prairie Rattlesnake (*Crotalus viridis viridis*) Venom, on Murine Skeletal Muscles", *Toxicon*, vol. 23, No. 6, pp. 927-937, 1985.

D.L. McKenzie et al, "A Potent New Class of Reductively Activated Peptide Gene Delivery Agents* ", *The Journal of Biological Chemistry*, vol. 275, No. 14, pp. 9970-9977, 2000.

G.R. Martin, "Isolation of a Pluripotent Cell Line from Early Mouse Embryos Cultured in Medium Conditioned by Teratocarcinoma Stem Cells", *Proc. Natl. Acad. Sci.*, vol. 78, No. 12, pp. 7634-7638, 1981.

C.L. Ownby et al, "Isolation of Myotoxic Component from Rattlesnake (*Crotalus viridis viridis*) Venom, Electron Microscopic Analysis of Muscle Damage", *Am. J. Pathol.*, pp. 149-158 w/illustrations, 1976.

J. Moura Gonçalves, "Studies about Poisons of Brazilian Serpents (*Crotalus terrificus crotaminicus*), Biological Subspecies", *An. da Acad. Brasileira de Ciências*, vol. 28, No. 3, pp. 365-367, 1956.

M.A. Sukoyan et al, "Establishment of New Murine Embryonic Stem Cell Lines for the Generation of Mouse Models of Human Genetic Diseases", *Brazilian Journal of Medical and Biological Research*, vol. 35, No. 5, pp. 535-542, 2002.

A. Wobus et al, "Pluripotent Mouse Embryonic Stem Cells are able to Differentiate into Cardiomyocytes Expressing Chronotropic Responses to Adrenergic and Cholinergic Agents and $Ca^{2+}$Channel Blockers", *Differentiation*, vol. 48, pp. 173-182, 1991.

A. Martin et al, "Herpes Simplex Virus Tegument Protein VP22 Contains Overlapping Domains for Cytoplasmic Localization, Microtubule Interaction, and Chromatin Binding", *Journal of Virology*, pp. 4961-4970, 2002.

M.J. Evans et al, "Establishment in Culture of Pluripotential Cells from Mouse Embryos", *Nature*, vol. 292, pp. 154-156, 1981.

D. Israel, "A PCR-Based Method for High Stringency Screening of DNA Libraries", *Nucleic Acid Research*, vol. 21, No. 11, pp. 2627-2631, 1993.

G. Fields et al, "Solid Phase Peptide Synthesis Utilizing 9-Fluorenylmethoxycarbonyl Amino Acids", *Int. J. Peptide Protein Res.*, vol. 35, pp. 161-214, 1990.

A. Kerkis et al, "Crotamine is a Novel Cell-Penetrating Protein from the Venom of Rattlesnake *Crotalus durissus terrificus", FASEB J.*, 18(12):1407-9, Epub. Jul. 1, 2004.

G. Nicastro et al, "Solution Structure of Crotamine, a Na+ Channel Affecting Toxin from *Crotalus durissus terrificus* Venom", *Eur. J. Biochem.*, 270(9): 1969-79, May 2003.

P. Lundberg et al, "A Brief Introduction to Cell-Penetrating Peptides", *J. Mol. Recognit.*, 16(5):227-33, Sep.-Oct. 2003.

May C Morris Current Opinion et al; Translocating Peptides and Proteins and Their Use for Gene Delivery; Current Opinion in Biotechnology 2000; pp. 461-466.

* cited by examiner

```
KA13 GGCACGAGCCAGAACCAGTCTCAGCATGAAGATCCTTTATCTGCTGTTCGCATTTCTTTTCCTT   64
KA19 GGCACGAGCCAGAACCAGTCTCAGCATGAAGATCCTTTATCTGCTGTTCGCATTTCTTTTCCTT   64
MK24 GGCACGAGCCAGAAC-AGTCTCAGCATGAAGATCCTTTATCTGCTGTTCGCATTTCTTTTCCTT   63
MK41 GGCACGA------------------GTGAAGATCCTTTATCTGCTGTTCGCATTTCTTTTCCTT   46
                              M  K  I  L  Y  L  L  F  A  F  L  F  L

MK9  GGCACGAG---GAACCAGTCTCAGCATGAAGATCCTTTATCTGCTGTTCGCATTTCTTTTCCTT   61
MK38 GGCACGAG---GAAC-AGTCTCAGCATGAAGATCCTTTATCTGCTGTTCGCATTTCTTTTCCTT   60
                              M  K  I  L  Y  L  L  F  A  F  L  F  L

KA13 GCATTCCTGTCTGAACCAGGGAATGCCTATAAACAGTGTCATAAGAAAGGAGGACACTGCTTT   127
KA19 GCATTCCTGTCTGAACCAGGGAATGCCTATAAACAGTGTCATAAGAAAGGAGGACACTGCTTT   127
MK24 GCATTCCTGTCTGAACCAGGGAATGCCTATAAACAGTGTCATAAGAAAGGAGGACACTGCTTT   126
MK41 GCATTCCTGTCTGAACCAGGGAATGCCTATAAACAGTGTCATAAGAAAGGAGGACACTGCTTT   109
      A  F  L  S  E  P  G  N  A  Y  K  Q  C  H  K  K  G  G  H  C  F

MK9  GCATTCCTGTCTGAACCAGGGAATGCCTATAAACAGTGTCATAAGAAAGGAGGACACTGCTTT   124
MK38 GCATTCCTGTCTGAACCAGGGAATGCCTATAAACAGTGTCATAAGAAAGGAGGACACTGCTTT   123
      A  F  L  S  E  P  G  N  A  Y  K  Q  C  H  K  K  G  G  H  C  F

KA13 CCCAAGGAGAAAATATGTATTCCTCCATCTTCTGACTTTGGGAAGATGGACTGTCGATGGAGA   190
KA19 CCCAAGGAGAAAATATGTATTCCTCCATCTTCTGACTTTGGGAAGATGGACTGTCGATGGAGA   190
MK24 CCCAAGGAGAAAATATGTATTCCTCCATCTTCTGACTTTGGGAAGATGGACTGTCGATGGAGA   189
MK41 CCCAAGGAGAAAATATGTATTCCTCCATCTTCTGACTTTGGGAAGATGGACTGTCGATGGAGA   172
      P  K  E  K  I  C  I  P  P  S  S  D  F  G  K  M  D  C  R  W  R

MK9  CCCAAGGAGAAAATATGTCTTCCTCCATCTTCTGACTTTGGGAAGATGGACTGTCGATGGAGA   187
MK38 CCCAAGGAGAAAATATGTCTTCCTCCATCTTCTGACTTTGGGAAGATGGACTGTCGATGGAGA   186
      P  K  E  K  I  C  L  P  P  S  S  D  F  G  K  M  D  C  R  W  R

KA13 TGGAAATGCTGTAAAAAGGGAAGTGGAAAATAATGCCATCTCCATCTAGGACCATGGATATCTT   254
KA19 TGGAAATGCTGTAAAAAGGGAAGTGGAAAATAATGCCATCTCCATCTAGGACCATGGATATCTT   254
MK24 TGGAAATGCTGTAAAAAGGGAAGTGGAAAATAATGCCATCTCCATCTAGGACCATGGATATCTT   253
MK41 TGGAAATGCTGTAAAAAGGGAAGTGGAAAATAATGCCATCTCCATCTAGGACCATGGATATCTT   236
      W  K  C  C  K  K  G  S  G  K stop

MK9  TGGAAATGCTGTAAAAAGGGAAGTGGAAAATAATGCCATCTCCATCTAGGACCATGGATATCTT   251
MK38 TGGAAATGCTGTAAAAAGGGAAGTGGAAAATAATGCCATCTCCATCTAGGACCATGGATATCTT   250
      W  K  C  C  K  K  G  S  G  K stop

KA13 CAAGATATGGCCAAGGACCTGAGAGTGCCGCCTGCTATCGCTTTATCTTTCTTTATCTAAATAAA 319
KA19 CAAGATATGGCCAAGGACCTGAGAGTGCCGCCTGCTATCGCTTTATCTTTCTTTATCTAAATAAA 319
MK24 CAAGATATGGCCAAGGACCTGAGAGTGCCGCCTGCTATTGCTTTATCTTTCTTTATCTAAATAAA 318
MK41 CAAGATATGGCCAAGGACCTGAGAGTGCCGCCTGCTATTGCTTTATCTTTCTTTATCTAAATAAA 301
MK9  CAAGATATGGCCAAGGACCTGAGAGTGCCGCCTGCTATCGCTTTATCTTTCTTTATCTAAATAAA 316
MK38 CAAGATATGGCCAAGGACCTGAGAGTGCCGCCTGCTATCGCTTTATCTTTCTTTATCTAAATAAA 315

KA13 ATTGCTACCTATCAAACGCTAAAAAAAAAAAAAAAAAAA----                       358
KA19 ATTGCTACCTATCA-ACGCTAAAAAAAAAAA-------------                      348
MK24 ATTGCTACCTATCAAACGCTAAAAAAAAAAAAAAAAAA-----                       356
MK41 ATTGCTACCTATCAAA----AAAAAAAAAAAAAAAAAAAAAAA                       340
MK9  ATTGCTACCTATCAAA----AAAAAAAAAAAAAAAAAAA----                       351
MK38 ATTGCTACCTATCAAA----AAAAAAAAAAAAAA---------                       345
```

FIGURE 4

SEQUENCE LISTING

```
<160> NUMBER OF SEQ ID NOS: 12

<210> SEQ ID NO 1
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Variable amino acid
<220> FEATURE:
<221> NAME/KEY: MOD_RES
<222> LOCATION: (5)..(10)
<223> OTHER INFORMATION: Variable amino acid
<220> FEATURE:
<221> NAME/KEY: MOD_RES
<222> LOCATION: (12)..(17)
<223> OTHER INFORMATION: Variable amino acid
<220> FEATURE:
<221> NAME/KEY: MOD_RES
<222> LOCATION: (19)..(29)
<223> OTHER INFORMATION: Variable amino acid
<220> FEATURE:
<221> NAME/KEY: MOD_RES
<222> LOCATION: (31)..(35)
<223> OTHER INFORMATION: Variable amino acid
<220> FEATURE:
<221> NAME/KEY: MOD_RES
<222> LOCATION: (38)..(42)
<223> OTHER INFORMATION: Variable amino acid
<220> FEATURE:
<223> OTHER INFORMATION: See specification as filed for detailed
      description of substitutions and preferred embodiments

<400> SEQUENCE: 1

Xaa Xaa Xaa Cys Xaa Xaa Xaa Xaa Xaa Xaa Cys Xaa Xaa Xaa Xaa Xaa
  1               5                  10                  15

Xaa Cys Xaa Xaa Xaa Xaa Xaa Xaa Xaa Xaa Xaa Xaa Xaa Cys Xaa Xaa
             20                  25                  30

Xaa Xaa Xaa Cys Cys Xaa Xaa Xaa Xaa Xaa
         35                  40


<210> SEQ ID NO 2
<211> LENGTH: 42
<212> TYPE: PRT
<213> ORGANISM: Crotalus durissus

<400> SEQUENCE: 2
```

```
Tyr Lys Gln Cys His Lys Lys Gly Gly His Cys Phe Pro Lys Glu Lys
  1               5                  10                  15

Ile Cys Leu Pro Pro Ser Ser Asp Phe Gly Lys Met Asp Cys Arg Trp
             20                  25                  30

Arg Trp Lys Cys Cys Lys Lys Gly Ser Gly
         35                  40


<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Gln Cys His Lys Lys Gly Gly His Cys Phe Pro Lys Glu Lys Ile
  1               5                  10                  15

Cys


<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Lys Met Asp Cys Arg Trp Arg Trp Lys Cys Cys Lys Lys
  1               5                  10


<210> SEQ ID NO 5
<211> LENGTH: 358
<212> TYPE: DNA
<213> ORGANISM: Crotalus durissus
<220> FEATURE:
<221> NAME/KEY: CDS
<222> LOCATION: (26)..(220)

<400> SEQUENCE: 5

ggcacgagcc agaaccagtc tcagc atg aag atc ctt tat ctg ctg ttc gca       52
                            Met Lys Ile Leu Tyr Leu Leu Phe Ala
                              1               5

ttt ctt ttc ctt gca ttc ctg tct gaa cca ggg aat gcc tat aaa cag      100
Phe Leu Phe Leu Ala Phe Leu Ser Glu Pro Gly Asn Ala Tyr Lys Gln
 10                  15                  20                  25

tgt cat aag aaa gga gga cac tgc ttt ccc aag gag aaa ata tgt att      148
Cys His Lys Lys Gly Gly His Cys Phe Pro Lys Glu Lys Ile Cys Ile
                 30                  35                  40

cct cca tct tct gac ttt ggg aag atg gac tgt cga tgg aga tgg aaa      196
Pro Pro Ser Ser Asp Phe Gly Lys Met Asp Cys Arg Trp Arg Trp Lys
             45                  50                  55

tgc tgt aaa aag gga agt gga aaa taatgccatc tccatctagg accatggata     250
Cys Cys Lys Lys Gly Ser Gly Lys
         60                  65

tcttcaagat atggccaagg acctgagagt gccgcctgct atcgctttat ctttctttat    310

ctaaataaaa ttgctaccta tcaaacgcta aaaaaaaaaa aaaaaaaa                 358


<210> SEQ ID NO 6
<211> LENGTH: 348
<212> TYPE: DNA
<213> ORGANISM: Crotalus durissus
```

-continued

<400> SEQUENCE: 6

```
ggcacgagcc agaaccagtc tcagcatgaa gatcctttat ctgctgttcg catttctttt     60
ccttgcattc ctgtctgaac cagggaatgc ctataaacag tgtcataaga aaggaggaca    120
ctgctttccc aaggagaaaa tatgtattcc tccatcttct gactttggga agatggactg    180
tcgatggaga tggaaatgct gtaaaaaggg aagtggaaaa taatgccatc tccatctagg    240
accatggata tcttcaagat atggccaagg acctgagagt gccgcctgct atcgctttat    300
ctttctttat ctaaataaaa ttgctaccta tcaacgctaa aaaaaaaa                 348
```

<210> SEQ ID NO 7
<211> LENGTH: 356
<212> TYPE: DNA
<213> ORGANISM: Crotalus durissus

<400> SEQUENCE: 7

```
ggcacgagcc agaacagtct cagcatgaag atcctttatc tgctgttcgc atttcttttc     60
cttgcattcc tgtctgaacc agggaatgcc tataaacagt gtcataagaa aggaggacac    120
tgctttccca aggagaaaat atgtattcct ccatcttctg actttgggaa gatggactgt    180
cgatggagat ggaaatgctg taaaaaggga agtggaaaat aatgccatct ccatctagga    240
ccatggatat cttcaagata tggccaagga cctgagagtg ccgcctgcta ttgctttatc    300
tttctttatc taaataaaat tgctacctat caaacgctaa aaaaaaaaaa aaaaaa        356
```

<210> SEQ ID NO 8
<211> LENGTH: 340
<212> TYPE: DNA
<213> ORGANISM: Crotalus durissus

<400> SEQUENCE: 8

```
ggcacgagtg aagatccttt atctgctgtt cgcatttctt ttccttgcat tcctgtctga     60
accagggaat gcctataaac agtgtcataa gaaaggagga cactgctttc ccaaggagaa    120
aatatgtatt cctccatctt ctgactttgg gaagatggac tgtcgatgga gatggaaatg    180
ctgtaaaaag ggaagtggaa aataatgcca tctccatcta ggaccatgga tatcttcaag    240
atatggccaa ggacctgaga gtgccgcctg ctattgcttt atctttcttt atctaaataa    300
aattgctacc tatcaaaaaa aaaaaaaaaa aaaaaaaaaa                          340
```

<210> SEQ ID NO 9
<211> LENGTH: 65
<212> TYPE: PRT
<213> ORGANISM: Crotalus durissus

<400> SEQUENCE: 9

```
Met Lys Ile Leu Tyr Leu Leu Phe Ala Phe Leu Phe Leu Ala Phe Leu
  1               5                  10                  15

Ser Glu Pro Gly Asn Ala Tyr Lys Gln Cys His Lys Lys Gly Gly His
             20                  25                  30

Cys Phe Pro Lys Glu Lys Ile Cys Ile Pro Pro Ser Ser Asp Phe Gly
         35                  40                  45

Lys Met Asp Cys Arg Trp Arg Trp Lys Cys Cys Lys Lys Gly Ser Gly
     50                  55                  60

Lys
 65
```

<210> SEQ ID NO 10

```
<211> LENGTH: 351
<212> TYPE: DNA
<213> ORGANISM: Crotalus durissus

<400> SEQUENCE: 10

ggcacgagga accagtctca gcatgaagat cctttatctg ctgttcgcat ttcttttcct     60

tgcattcctg tctgaaccag ggaatgccta taaacagtgt cataagaaag gaggacactg    120

ctttcccaag gagaaaatat gtcttcctcc atcttctgac tttgggaaga tggactgtcg    180

atggagatgg aaatgctgta aaaagggaag tggaaaataa tgccatctcc atctaggacc    240

atggatatct tcaagatatg gccaaggacc tgagagtgcc gcctgctatc gctttatctt    300

tctttatcta aataaaattg ctacctatca aaaaaaaaaa aaaaaaaaaa a             351


<210> SEQ ID NO 11
<211> LENGTH: 345
<212> TYPE: DNA
<213> ORGANISM: Crotalus durissus
<220> FEATURE:
<221> NAME/KEY: CDS
<222> LOCATION: (22)..(216)

<400> SEQUENCE: 11

ggcacgagga acagtctcag c atg aag atc ctt tat ctg ctg ttc gca ttt       51
                        Met Lys Ile Leu Tyr Leu Leu Phe Ala Phe
                          1               5                  10

ctt ttc ctt gca ttc ctg tct gaa cca ggg aat gcc tat aaa cag tgt       99
Leu Phe Leu Ala Phe Leu Ser Glu Pro Gly Asn Ala Tyr Lys Gln Cys
                 15                  20                  25

cat aag aaa gga gga cac tgc ttt ccc aag gag aaa ata tgt ctt cct      147
His Lys Lys Gly Gly His Cys Phe Pro Lys Glu Lys Ile Cys Leu Pro
             30                  35                  40

cca tct tct gac ttt ggg aag atg gac tgt cga tgg aga tgg aaa tgc      195
Pro Ser Ser Asp Phe Gly Lys Met Asp Cys Arg Trp Arg Trp Lys Cys
         45                  50                  55

tgt aaa aag gga agt gga aaa taatgccatc tccatctagg accatggata         246
Cys Lys Lys Gly Ser Gly Lys
     60                  65

tcttcaagat atggccaagg acctgagagt gccgcctgct atcgctttat ctttctttat    306

ctaaataaaa ttgctaccta tcaaaaaaaa aaaaaaaaa                           345


<210> SEQ ID NO 12
<211> LENGTH: 65
<212> TYPE: PRT
<213> ORGANISM: Crotalus durissus

<400> SEQUENCE: 12

Met Lys Ile Leu Tyr Leu Leu Phe Ala Phe Leu Phe Leu Ala Phe Leu
  1               5                  10                  15

Ser Glu Pro Gly Asn Ala Tyr Lys Gln Cys His Lys Lys Gly Gly His
             20                  25                  30

Cys Phe Pro Lys Glu Lys Ile Cys Leu Pro Pro Ser Ser Asp Phe Gly
         35                  40                  45

Lys Met Asp Cys Arg Trp Arg Trp Lys Cys Cys Lys Lys Gly Ser Gly
     50                  55                  60

Lys
 65
```

METHODS, KITS AND COMPOSITIONS COMPRISING CROTAMINE

CROSS-RELATED APPLICATIONS

This application is a continuation of International Patent Application No. PCT/BR2006/000052, filed Mar. 17, 2006, which claims the benefit of priority of Patent Application No. PI0501037-3, filed Mar. 18, 2005. The disclosures of the prior applications are hereby incorporated in their entirety by reference.

FIELD OF THE INVENTION

The present invention refers, in one aspect, to the uses of crotamine and compositions containing it, based on its novel characteristics of internalization into cytoplasm and nucleus of mammalian cells carrying genetic material and other biological molecules, which can be associated with crotamine.

In one of its aspects, the invention refers to a series of applications of crotamine in submicromolar amounts, in which the concentration range of this polypeptide is no longer toxic, based on its characteristics of cell penetration, molecule transport to the surface, cytoplasm or cell nucleus, with a particular selectivity for actively proliferating cells.

According to the invention, more particularly but not excluding any other form, crotamine and compositions containing it are appropriate, e.g., for the following practical uses in the diagnosis, pharmaceutical and biotechnological area:

for the delivery of molecules inside a cell, in vitro or in vivo; and for the identification and/or specific tagging of actively proliferating cells in a mixed cell population, in vitro or in vivo.

In another aspect, the invention refers to compositions comprising a pharmaceutically effective concentration of crotamine and their use for the treatment of diseases and dysfunctions, based on its characteristics of interaction with genetic material, such as DNA and RNA, and other biological molecules, which can be associated with crotamine. and its cell selectivity.

BACKGROUND OF THE INVENTION

Toxicity

To the eyes of an expert in the art, and bearing in mind the knowledge in the state of the art, the toxic characteristics of crotamine may inhibit studies aiming its use for any beneficial purpose for human beings and other living organisms.

Crotamine is a toxin, more specifically a myotoxin, isolated from the venom of South American rattlesnake, *Crotalus durissus terrificus*. This toxin is one of the most abundant component in the venom of rattlesnake, corresponding to approximately 10% of dry weight of the crude venom. Crotamine is a basic polypeptide with a low molecular weight of about 4,800 Daltons, with isoelectric point above 9.5. It is constituted by 42 amino acid residues (YKQCHKKGGHCF-PKEKICLPPSSDFGKMDCRWRWK CCKKGSG (SEQ ID NO: 2)), showing six cysteine residues forming three disulphide bridges, and it is rich in basic amino acids, such as lysine and arginine.

When injected intraperitoneally, crotamine causes a quick paralysis, in less than 15 minutes, of the hind legs of mice, which is the typical physiological effect of this toxin. Furthermore, difficulty in breathing and rigidity are also observed, suggesting veratrine-simile action (Gonçalves, J. M. (1956), as mentioned above. At cellular and molecular levels, crotamine induces an increase in the voltage-dependent sodium current (as mediated by sodium channels) by causing high depolarization (reduction of rest potential) of the membrane of myocites of muscle fibers next to motor plates—a mechanism which is prevented by tetradotoxin (TTX). Consequently, the massive inflow of sodium ions causes dilatation of the sarcoplasmatic reticulum of myocites and the slow induction of myonecrosis restricted to the cells of skeletal muscles.

This mechanism, through which crotamine exerts its toxicity, is similar to that described for myotoxin-a from *Crotalus viridis viridis*, a more extensively studied toxin.

Crotamine is able to form dimers through linkages between disulphide chains, acquiring a form close to a sphere, which covalently links extra subunits.

Therefore, there are no publications in the state of the art suggesting or indicating, in any form, benefits incurred from the effects of crotamine on living organisms.

Cell Penetration

Cell-penetrating peptides (CPP, or "cell-translocating peptides") are known in the state of the art. A few characteristics of this type of peptide were already published, such as its cationic character, low molecular weight and high content of basic amino acids. But these peptides may vary in their primary structure, size and/or ability to penetrate cells, which makes it difficult to recognize a CPP. The basic structural characteristic leading to the cell penetration feature is still unknown. Some natural CPPs have been described, for instance, the protein HIV-1 TAT, derived from the human immunodeficiency virus (HIV-1) and isolated from the virus transcription activation factor, it shows the ability to penetrate into cells in vitro, with a cytoplasmic and nuclear localization; $Antp_{43-58}$, derived from the transcription factor of the Antennapedia homeodomain from *Drosophila*; and also the structural protein of Herpes simplex virus type 1 (HSV-1), named as VP22. These three cell-penetrating proteins have protein transduction domains (PTDs), i.e., a sequence of amino acid residues that in the isolated form presents a higher cell penetration efficiency.

However, even considering the few standard common structural characteristics of a cell-penetrating peptide, a skilled man in the art would not be able to predict the effect of the presence of the three disulphide bonds of crotamine in the cell-penetrating property. These disulphide bonds are formed by six cysteines present in crotamine molecule, and is one of the structural characteristics that distinguishes it from other known natural cell-penetrating peptides.

Transport of Molecules to Cytoplasm and Cell Nucleus

In the state of the art, few technologies on the transport of genetic material to the cytoplasm and/or cell nucleus are known, but they all present a few shortcomings, such as the lack of cell selectivity and low efficiency of molecule loading. The use of cationic peptides isolated from snake venom for these purposes, such as crotamine, has never been published before.

References covering the subject, as generically associated to this aspect of the invention (intracellular and nuclear penetration and/or DNA and/or molecule transport), are all of them different from the present invention and none of them indicate nor suggest in any form, any feature of the crotamine, as described by the Applicant herein.

The U.S. Pat. No. 4,774,318 discloses the isolation of a small polypeptide with cytotoxic activity, purified from the low molecular weight fraction of the rattlesnake *Crotalus atrox*. This compound may be used as an inhibitor for cell growth, both pure and in combination with other reagents, such as antibodies. Conjugates of these peptides with specific binding members, e.g., ligands and receptors, may be used for selectively removing cells from a mixture of cells.

The U.S. Pat. No. 6,420,176 discloses a composition for DNA transfer to antigen presenting cells. A molecular complex for a specific transfer to antigen presenting cell is formed by a non-viral gene transfer system complexed with a foreign genetic material. The complex then enters the target cell through specific receptors and shows resistance to the intracellular degradation mechanisms. Consequently, the incorporation or transduction of said foreign genetic material results in the expression of the corresponding protein. The patent also includes a gene immunization method without using needles.

The U.S. Pat. No. 6,461,641 discloses a delivery techniques of therapeutic reagents for tumor treatment. The main problem of usual methods for the delivery of therapeutic reagents, into solid tumors, specially of cells or large volumes of recombinant DNA reagents or drugs, has been the resistance of said tissues to the influx of cells and/or fluids, resulting in a low efficiency of the fluid and/or cell penetrating into and remaining in the tumor tissues to be treated. The use of more viscous vehicle, preferably with similar density of the tissue, allows more efficient penetration and reduced backflow and diversion through the point of entry, so that more material may be introduced and remains in the tumor. Preferred materials include solutions or suspensions of a polymeric material which gel or solidify at the time of or shortly after injection or implantation.

The U.S. Pat. No. 6,635,623 discloses lipoprotein as a vector for the transport of nucleic acids. This invention relates to the materials and methods for the transport and conduction of nucleic acids in vivo. It specifically refers to the use of lipoproteins, including low density lipoproteins (LDL) and/or as apolipoproteins, to bind and transport nucleic acids in vivo. Furthermore, this invention refers to the use of lipoproteins for the early detection of cancer and/or metastasis and/or arteriosclerosis.

The U.S. Pat. No. 6,638,767 discloses methods to deliver compounds into the cells by using organic halides and/or carriers, which may be associated with the use of ultrasound. Organic halide is defined as a halogenated organic compound, i.e., containing at least one carbon atom and at least one halogen atom which may be fluorine (preferably), chlorine, bromine or iodine.

The U.S. Pat. No. 6,676,935 discloses tissue-specific adenovirus as a deliver agent for transfecting target host cell. By providing for transcriptional initiating regulation dependent upon transcription factors which are only active for specific and restricted cell types, viral replication may be restricted to target cells. Modified adenovirus may be used as a carrier for introducing the genetic material, particularly associated with cytotoxicity for treating neoplasia.

The U.S. Pat. No. 6,680,301 discloses a method for transferring molecules to cells by disrupting endosomal and lysosomal membranes using photodynamic treatment, without killing the majority of the cells by the photodynamic treatment. More specifically, this invention includes a DNA and/or RNA transfer method, such as genes, to cells by photochemically inducing the disruption of endosomes and lysosomes.

The U.S. Pat. No. 6,692,911 discloses a composition to deliver compounds inside cells and specifically refers to biocompatible endosomolytic agents. In an ideal formulation, endosomolytic agents are biodegradable and may disintegrate within cells into compounds which may be re-used or released by the cell. Endosomolytic agents include cationic polymers, specifically compounds constituted by biomolecules, such as histidine, poly-histidine, poly-lysine or any combination thereof. Another example of an endosmolytic agent includes imidazole-containing compounds such as vinylimidazole and histamine. Agents having multiple proton acceptor sites and acting as a "proton sponge", disrupting the endosome by osmolytic action. In preferred embodiments, this patent also contemplates the use of these endosomolytic agents as delivery agents by complexation with the desired compound to be delivered.

The known methods used for intracellular DNA delivery may be basically classified as viral and non-viral systems. It should be considered that the efficiency in DNA transport depends on steps such as: the absorption of the transfection complex in contact with the cell surface, internalization of said complex by the cell, release from the endosomes and translocation to the nucleus for gene expression. Viral carriers are able to overcome all these obstacles, since they express proteins that facilitates the gene transportation through these several levels. However, these vectors present limited DNA transport ability, besides several shortcomings, such as, problems in the packaging and production process, risk of viral recombination, toxicity and immunogenicity in vivo. On the other hand, although the non-viral carriers appear as powerful tools to elucidate gene function and regulation, they present low efficiency for DNA delivery to the nucleus of the target cells. The non-viral system is safer than the viral system and it has been currently used for clinical tests, but its low efficiency in the transgene expression remains to be its main disadvantage. However, crotamine, as a non-viral carrier, as described in the present invention, shows a surprisingly effective DNA delivery to the cytoplasm and/or to the cell nucleus in vitro and mainly in vivo.

Therefore, the uses of crotamine, as described in the present invention, could not be foreseen so far, and they have never been disclosed or suggested in the state of the art, including the lack of toxicity at lower concentrations, the ability to penetrate cells or transport of genetic material or other molecules to the surface, cytoplasm or cell nucleus, besides its surprising selectivity for actively proliferating cells.

BRIEF DESCRIPTION OF THE DRAWINGS

FIG. 4 shows the amino acid sequence deduced from the cDNA nucleotide sequence coding for the precursor of crotamine isoforms. FIG. 4 discloses SEQ ID NOS 5-12, respectively, in order of appearance.

A-D) Internalization of Cy3-crotamine, 3 h after injection into mice, observed in nuclei and perinuclear space of peritoneal liquid cells. A) Cy3-crotamine. B) Nuclei stained by DAPI. C) Superimposed images (A) and (B): partial overlapping of Cy3-crotamine localization and DAPI staining in nuclei. D) Superimposed images (A) and (B), demonstrating overlapping of Cy3-crotamine localization and DAPI staining within the nuclei, and overlapping of cytoskeleton immunostained with anti-tubulin antibody and Cy3-crotamine in perinuclear space (A–D=Epifluorescence, EF; bar=50 μm). E-G) Cy3-crotamine strong labeling in nucleus (asterisk) and weak fluorescence in cytoplasm of mouse megakaryocyte (E=Dic, F=Fcm, G=Dic+Fcm; bars=25 μm). H) Cells pretreated with non-labeled crotamine followed by Cy3-crotamine treatment. Strong fluorescence restricted to the cytoplasm indicates saturation of binding sites by non-labeled crotamine in the nucleus (asterisk), as clearly observed in the megakaryocyte (Dic+Fcm; Bar=10 μm). I-K) Metaphase of lymphoblastic cell. (EF; Magnification, 800×). I) Cy3-crotamine labeled chromosomes. A banding pattern is produced as shown by the chromosome in the inset. J) DAPI-stained chromosomes. K) Superposition of images (I) and (J): Crotamine labeling is observed on DAPI-stained chromosomes. In the inset, the association of crotamine with DAPI-stained chromosomes is depicted (arrow).

Figure 6:
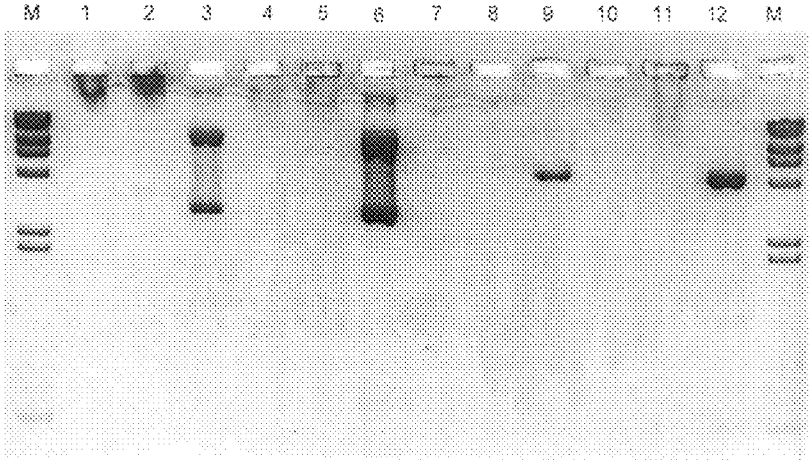

FIG. 6 shows the analysis of the DNA-peptide interaction by agarose gel electrophoresis. This electrophoresis system allows to observe changes in migration pattern (delay in migration) due to the neutralization of the nucleic acid charges by the cationic peptide present and/or due to the formation of larger complexes between crotamine and DNA.

Figure 7:
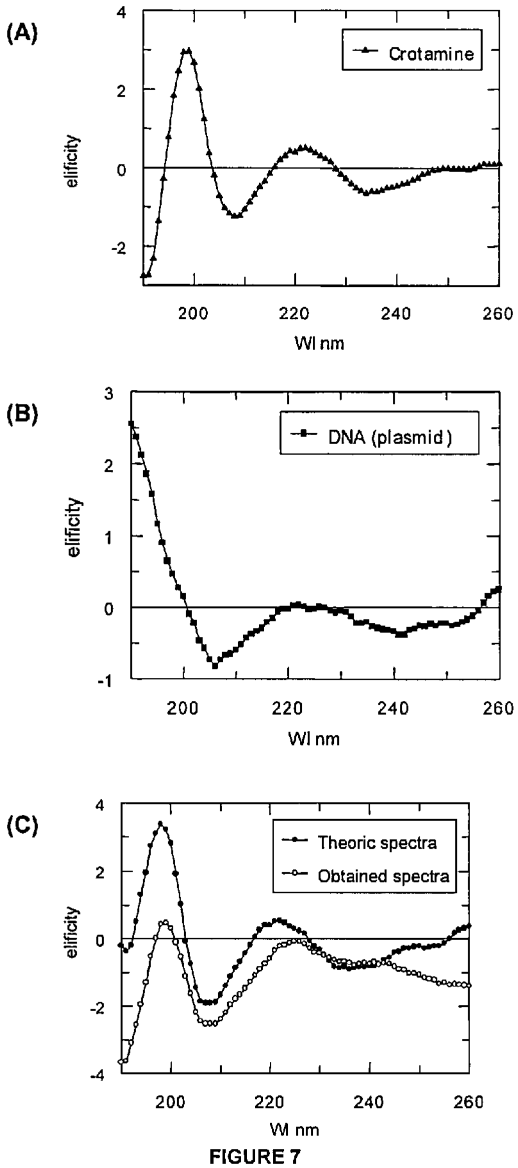

FIG. 7 shows the analysis of the DNA-peptide interaction by circular dichroism. Panel (A) shows circular dichroism spectra of crotamine 20 μM and panel (B) shows circular dichroism spectra of plasmidial DNA 0.1 μM. Panel (C) shows the spectrum observed by mixing crotamine 20 μM with the plasmidial DNA 0.1 μM, which differs from the theoretical spectrum as obtained by the sum of spectra of panels (A) and (B).

Figure 8:
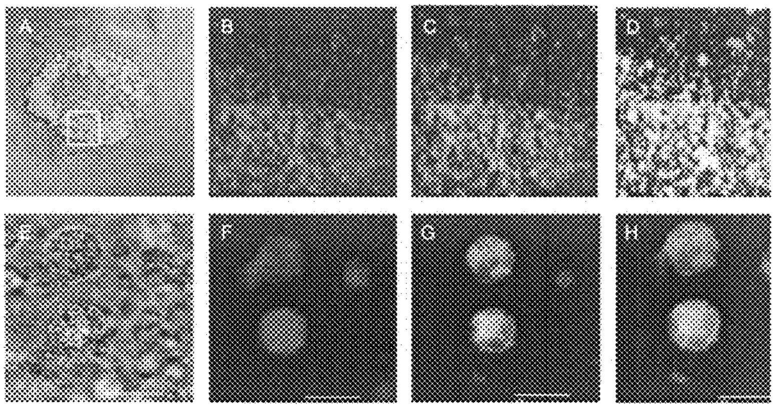

FIG. 8 shows the internalization of crotamine in actively proliferating cells. (A) shows the internalization of crotamine in ES cells during the differentiation process; (B-D) show the amplification of the region limited by the square in (A), (B) shows the internalization of Cy3-crotamine in actively proliferating cells, (C) shows the incorporation of BrDU in actively proliferating cells and (D) shows the overlaying of images (B) and (C); (E-H) shows three ES cells showing the co-location of crotamine with the staining by the BrDU in actively proliferating cells, (E) shows digital interference contrasts of actively proliferating cells, (F) shows the internalization of Cy3-crotamine in actively proliferating cells, (G) shows the incorporation of BrDU in actively proliferating cells and (H) shows the overlaying of images (F) and (G).

Figure 9:
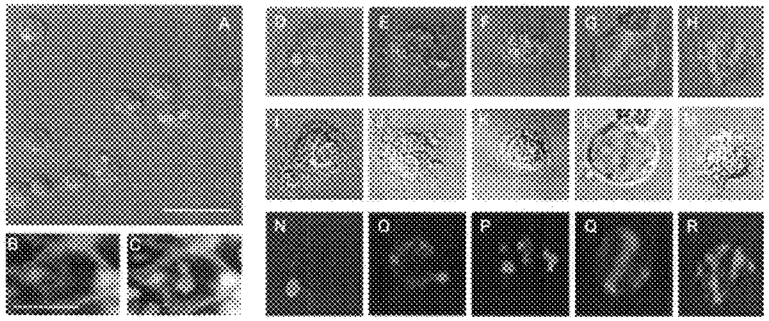

FIG. 9 shows the association between Cy3-crotamine and centrioles. A) Peritoneal liquid cells showing Cy3-crotamine fluorescence on centrosomes (arrowheads). (Dic+Fcm; bar=100 μm). B) Microtubules and esters (arrowheads) immunolabeled by anti α-tubulin in pluripotent ES cell. C) Superimposed images of centrioles labeled by Cy3-crotamine and esters immunolabeled by anti α-tubulin: the labeling of the centrioles results from the superposition of labels). Chromosomes are strongly labeled by crotamine. (B, C=Fcm; bars=10 μm). D-R) Centriole labeling (arrowheads) by Cy3-crotamine in peritoneal liquid cells. D,I,N) In G1 phase, pericentriolar material associated with a pair of centrioles is strongly labeled by crotamine. E,J,O) In S/G2 phase the duplicated centriolos start to separate. Fluorescence is also observed in the cell nucleus. F,K,P) In prophase, the two centrioles are moving to opposite poles. Crotamine binding to chromosomes becomes evident. G,L,Q) In metaphase and (H,M,R) anaphase strong fluorescence is observed on centrioles and on chromosomes.

Figure 10:
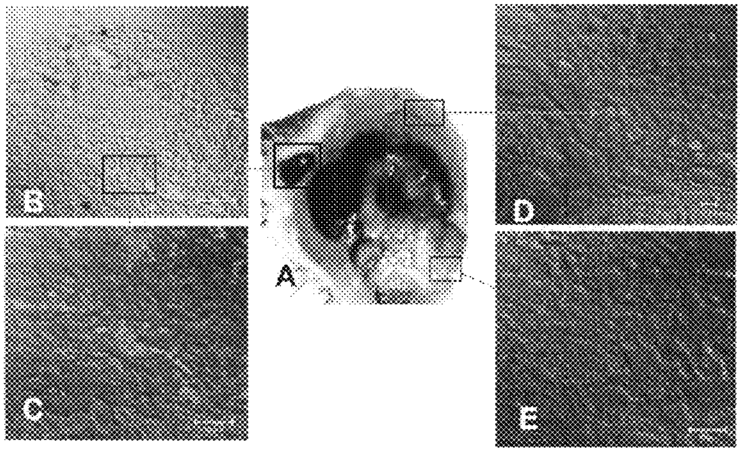

FIG. 10 shows the Cy3-crotamine labeling of actively proliferating cells observed 5 days after subcutaneous injection of B16 cells into mice. A) Histological section, tumor are presented by black cells. B) and C) Cy3-crotamine (red) in solid tumor (C-higher magnification of B). D) Cy3-crotamine labeled metastases observed around the tumor. E) Normal cells as a control.

DETAILED DESCRIPTION OF THE INVENTION

Studies performed by the inventors disclose properties not described before providing new applications for crotamine, i.e.:

- to be a cell-penetrating peptide;
- non-toxic under submicromolar concentrations; and
- ability to transport molecules to the cell (to the external surface of the cell, to within the cytoplasm or even into its nucleus), be it in vitro or in vivo.

Additionally, crotamine presents said qualities more efficiently than other CPPs, as known in the state of the art.

We can also verify that, differently from other CPPs, crotamine shows a cellular selectivity and being specific for actively proliferating cells, it has a preferential use for this purpose.

The invention therefore deals, in a first aspect, with uses of crotamine, useful, e.g., for diagnostic, pharmaceutical and/or biotechnological areas, e.g., as mentioned below:

- carrier of molecules of interest to the cell surface, cytoplasm or cell nucleus, particularly molecules constituted by nucleic acids or their analogues of modified ones, such as plasmid DNA, RNA, ribozymes, siRNA, decoy DNA and RNA, DNAzymes; proteins, peptides or any other chemical conjugated or covalently linked to crotamine; and
- identification or specific tagging of actively proliferating cells, particularly tumor or stem cells, in a mixed cell population, in vitro or in vivo.

Examples of the use of crotamine as a carrier of genes of interest to the nucleus of a cell are as follows:

- gene delivery system in cell therapy and transgenesis; and
- DNA vaccines, usually in plasmid form, having a gene codifying an antigenic protein to be expressed and produced in cells of a vaccinated mammal. Also designated as third generation vaccines, DNA vaccines are tools allowing to induce in the organism similar effects caused by a natural infection and the desired immune response.

According to the invention, there are biotechnological uses of crotamine in experimental area, particularly as a reagent for the cell transfection. We also highlight, in the experimental area, the use of crotamine for the specific identification of precursors and stem cells in a homogeneous and/or mixed cell cultures. We can particularly mention its use in efficient isolation of stem cells, e.g., from bone marrow and umbilical cord, which is required for their future employment in therapy. Currently, the said isolated cultures contain other types of cells besides stem cells, due to the lack of an efficient selection processes. Since crotamine presents selection specificity for actively proliferating cells, particularly stem cells and tumor cells, crotamine can be used as a precise marker for said cells in said selection processes.

Use of Functional Equivalents

In the present invention, the mention of crotamine is also understood to cover its functional equivalents, i.e., structurally different molecules, fragments, analogues, derivatives and associates, but performing the same function and showing similar characteristics. This means that changes made by a skilled person in the art, with a common knowledge to those of ordinary skill in the art, which obviously leads to equivalent effects, are also embodiments of the invention.

As examples, however, merely intended to illustrate the embodiments of the invention and not to limit the scope of the invention, possible modifications of crotamine are shown based on the knowledge as disclosed herewithin, which is common to those of skill in the art in the present state of the art.

Crotamine is a 42-amino acid oligopeptide and it may be expressed by SEQ ID No. 1, as follows:

$aa^1aa^2aa^3C^4aa^5aa^6aa^7aa^8aa^9aa^{10}C^{11}aa^{12}aa^{13}aa^{14}aa^{15}$ $aa^{16}aa^{17}C^{18}aa^{19}aa^{20}aa^{21}aa^{22}aa^{23}aa^{24}aa^{25}aa^{26}aa^{27}$ $aa^{28}aa^{29}C^{30}aa^{31}aa^{32}aa^{33}aa^{34}aa^{35}C^{36}C^{37}aa^{38}aa^{39}aa^{40}$ $aa^{41}aa^{42}$ wherein aa means a specific amino acid residue and C means cysteine.

A skilled person in the art knows how to substitute a specific amino acid by others, but keeping the same features, or equivalent alternative characteristics of that described for natural crotamine (even by knowledge of the state of the art or by regular experience in the field). In such a way, that the effects observed for natural crotamine, as disclosed by this invention, is maintained. More specifically, the basic characteristics of crotamine and its equivalents, according to the present invention, are: low toxicity, cell penetration ability and ability to carry molecules to the surface, cytoplasm or cell nucleus. Preferentially and more particularly, crotamine also presents the characteristic to act selectivity on actively proliferating cells, such as stem cells and tumor cells.

A few examples merely intended to illustrate the embodiments of the invention and not to limit the scope of the invention, are mentioned below:

Cysteines may or not form intramolecular disulphide bonds.

Cysteine (C) may be substituted with similar compounds, such as homocysteine, penicilamine or serine.

$aa^{1-3}$ are respectively Y, K and Q, but may be substituted with others, independently basic or non-carried polar.

$aa^{5-10}$ are respectively H, K, K, G, G and H, but may be substituted with others, independently basic or non-polar.

$aa^{12-17}$ are respectively F, P, K, E, K and I, but may be substituted with others, independently basic, acid or non-polar.

$aa^{19-29}$ are respectively L, P, P, S, S, D, F, G, K, M and D, but may be substituted with others, independently basic, acid, non-carried polar or non-polar.

$aa^{31-35}$ are respectively R, W, R, W and K, but may be substituted with others, independently basic or non-polar.

$aa^{38-42}$ are respectively K, K, G, S and G, but may be substituted with others, independently basic, non-carried polar or non-polar.

In the above statements, the following one-letters code for amino acids are used:

E—glutamic acid
A—alanine
R—arginine
D—asparagine
F—phenylalanine
G—glycine
Q—glutamine
H—hystidine
I—isoleucine
L—leucine
K—lysine
P—proline
S—serine
Y—tyrosine
T—threonine
W—tryptophan
V—valine As known by the expert in the art, amino acid residues (aa) can be in L or D-configurations, and be substituted with derivatives with equivalent characteristics, such as (three-letter codes are listed for each one):

aminobutyric acid (Abu)
aminoisobutyric acid (Aib)
diaminobutanoic acid (Dab)
diaminopropionic acid (Dpr)
hexaenoic acid (ε-Ahx)
isonipecotic acid (Isn)
tetrahydroisoquinoline-3-carboxylic acid (Tic)
butyl-glycinocyclohexylalanine (Cha)
citruline (Cit)
statine and derivatives (Sta)
phenylglycine (Phg)
hydroxyproline (Hyp)
homoserine (Hse)
norleucine (Nle)
norvaline (Nva)
ornithine (Orn)
penicilalanine (Pen)
sarcosine (Sar)
iethylalanine (Thi)

Thus, compounds equivalent to crotamine, their fragments and derivatives, protected by the present invention, are oligopeptides or peptides with a particularly defined sequence of amino acid residues in which each amino acid residue may be substituted with another equivalent one, leading to a change in the structural feature, but keeping the same function and similar effects. Equivalent amino acid residues are those keeping the same biochemical nature of the side chains:

acids: the residue presents negative charge due to the loss of hydrogen ion (H) under physiological pH, and this residue is attracted by the water solution of the medium;

basics: the residue has positive charge due to the addition of a hydrogen ion (H) under physiological pH, and this residue is attracted by the water solution of the medium;

hydrophobic or apolar neutral: the residues do not present net charge, therefore neutral, under physiological pH, and these residues are water-repelling and tend to interact with one another and other hydrophobic groups;

non-charged polar: the residues do not present net charge and neutral under physiological pH, some of neutral amino acids are polar because of the distribution of charges within the molecule, and are not efficiently repelled by the water.

Crotamine, according to the present invention, may be under dimeric or monomeric form, containing or not disulphide bridges.

Another alternative embodiment of the invention refers to compositions comprising crotamine under pharmacologically effective concentration, preferably in an amount ranging from about 100 μM to about 0.01 μM, more preferably from about 1 μM to about 0.1 μM. The composition also comprises other appropriate compounds, excipients, vehicles such as genes, genetic material or molecules of interest, particularly those constituted by nucleic acids or modified analogues, such as plasmid DNA, RNA, ribozymes, siRNA, decoy DNA and RNA, DNAzymes; or proteins or peptides, or drugs of interest only complexed with, conjugated or even covalently linked to crotamine.

Another aspect of the invention refers to a kit. In an alternative embodiment, said kit comprises crotamine as a reagent to transfect or carry molecules to the cytoplasm or cell nucleus. In another embodiment, said kit comprises crotamine as a reagent to identify and select actively proliferating cells from a mixed cell population, particularly from the umbilical cord and/or bone marrow.

A particular composition of the present invention is injectable, e.g., to be administered parentally, subcutaneously, intramuscularly, intravenously, intraarterially or intraperitoneally.

EXAMPLES

The present invention will be more fully understood by reference to the following examples. These examples, however, are merely intended to illustrate the embodiments of the invention and are not to be construed to limit the scope of the invention, as presented further below.

Example 1

Isolation and Purification of Crotamine from the Venom of *Crotalus durissus terrificus*

A—Purification of Crotamine by Chromatography

The toxin of *Crotalus durissus terrificus* was extracted and dried under vacuum. 600 mg of total venom were dissolved in 5 ml of 0.25 M ammonium formate (pH 3.5) and crotoxine, which constitutes the largest component of the venom, was precipitated by the slow addition of 20 ml of ice water and centrifuged out. The 1 M Tris-base buffer was added drop by drop to the supernatant until reaching pH 8.8 and the solution was applied to a CM-Sepharose FF column (1.5×4.5 cm; supplier: Amersham-Pharmacia) equilibrated with 0.04 M Tris-HCl buffer, pH 8.8, containing 0.064 M NaCl. After washing the column with 100 ml of the equilibrated solution, crotamine was collected as a sharp peak by increasing NaCl concentration up to 0.64 M. The collected fraction was dialyzed by using a benzoylated membrane with a cut off of MW 3,000 and lyophilized. The amino acid analysis of purified crotamine after the acid hydrolysis (4N $MeSO_3H$+0.1% triptamine; 24 hours at 115° C.) indicated a yield of 72 mg with a purity higher than 98%.

B—High Performance Liquid Chromatography—HPLC

Crotamine was isolated and purified by high performance liquid chromatography (HPLC), Merck-Hitachi model L-6200A, with a visible UV detector adjusted for detection at 214 nm, coupled to a reverse phase column: C-18/Beckman (4.6×250 mm/5μ resin) using as solvents: solvent A, 0.1% TFA/$H_2O$ and solvent B, 10% solvent A/acetonitrile (ACN); 5% to 60%, with 0.5 ml/min flow, and the gradient used varying according to the sample. Peptide samples are manually separated from the effluent according to the shape of peaks, as monitored by absorbance at 214 nm.

Example 2

Determination of the Molecular Mass and Primary Structure of Crotamine by Mass Spectrometry (Es-Ms-Ms)

A method to determine the amino acid sequence of crotamine purified from the venom of rattlesnake, more specifically *Crotalus durissus terrificus*, by mass spectrometry analysis, is performed by using the mass spectrometer, model Micromass Quattro II (ESMS-MS/Micromass) in the positive ionization mode, equipped with Electrospray soured (Micromass). The software suite includes Mass Lynx (Micromass) for data acquisition; it comprises the following steps: samples dissolved in 50% $H_2O$/ACN with 0.1% formic acid, and introduced into machine with an injection pump under constant flow of 5 μl/min, and data acquired in the first quadruple (ESMS) by scanning the mass/load ratio (m/z) from 400 to 1600, using scanning time of five seconds for the whole analysis process, sequence determined by peptide selection with a protoned ion characterized in the first quadruple, followed by fragmentation made by collision by induced dissociation (CID) with argon gas pressure of $3\times10^{-3}$ Torr, and the data finally acquired by scanning in the second quadruple (ESMS-MS). The software Mass Lynx (Micromass) was used to control data acquisition.

Another form of purification, followed by characterization and sequencing, is made by using the HPLC system coupled to the mass spectrometry system (LC-ESMS-MS), where HPLC, Hewlett-Packard model 1100 was used, with automatic injector and visible UV detector, adjusted at 214 nm, where the reverse phase column was used: C-18/The Separations Group (4.6×250 mm/φ 5μ) to isolate the components of the total venom. The used solvents were: Solvent A: 0.1% TFA/$H_2O$-Solvent B: 10% solvent A/ACN, with 0.6 ml/min flow. The used gradient was:

t=0 min to 5 min: 0% B
t=5 min to 65 min: 0% to 60% B
t=65 min to 70 min: 60% to 100% B
t=70 min to 75 min: 100% B
t=75 min to 80 min: 100% to 0% B From the flow used at HPLC of 600 μl/min, 20 μl were automatically introduced into the mass spectrometer and the remaining 580 μl to the visible UV detector.

Mass spectrometry analyses were made on the mass spectrometer Micromass Quattro II (ESMS-MS/Micromass) under the positive ionization mode equipped with Electrospray source (Micromass). The acquisition of characterization and sequencing data was made by the use of the software Mass Lynx (Micromass).

Example 3

Determination of the Amino Acid Sequence of Crotamine Deduced from the cDNA of the precursor of said molecule as expressed in snake tissues, Specifically *Crotalus durissus terrificus*, Comprising the Following Steps A—Purification of Messenger RNA and Construction of cDNA Library from a Venom Gland of *Crotalus durissus terrificus*

The total RNA from the venom gland of *Crotalus durissus terrificus* was isolated by the extraction method using the reagent Trizol (Invitrogen) containing guanidine isothiocianate—phenol-chloroform. The corresponding messenger RNA was purified by double passage through a pre-packed oligo-dT cellulose column (Invitrogen). An aliquot of the messenger RNA obtained was submitted to denaturing agarose gel electrophoresis (containing 1% to 2.5% formaldehyde) and stained with ethidium bromide to visualize and for qualitative analysis of the RNA sample.

Subsequently, RNA was transferred to nylon membranes for checking the integrity of RNA samples to be confirmed through hybridizations with specific probes. The construction of a cDNA library in λ ZAP phages was obtained by using the library construction kit commercialized by Stratagene (La Jolla Calif., U.S.A.). After cloning into the λ ZAP phages, the double strand cDNA inserts obtained from 5 μg of the total messenger RNA from the venom gland, these were packed in vitro and subsequently titered to verify cloning efficiency. Said phage library was then amplified and aliquots were stocked at −20° C. and −80° C. under the presence of chloroform or DMSO, respectively.

B—cDNA Amplification from the Total Phage Lysate

By using the total phage lysate (10 μl) from the cDNA library, PCR (Polymerase Chain Reaction) amplification reactions were made by using specific oligonucleotides, designed from the cDNA sequence codifying the crotamine precursor from the venom gland. Phage lysate was initially incubated at 100° C. for five minutes and cooled at 4° C., followed by the addition of other amplification reaction components, constituted by 30 pmol of each specific primer, 0.58 U of Taq DNA polymerase (5000 U/ml—Invitrogen), 200 μM dNTPs, 3.5 mM $MgCl_2$ and 1×PCR buffer, supplied together with the enzyme. Reactions thus prepared were submitted to a denaturation cycle at 94° C. for four minutes and subsequently to 30 cycles of 94° C. for 1 min, 43° C. for 45 seconds and 72° C. for one minute. At the end of said cycles, reactions were maintained at 4° C. The analysis of the generated products was done by agarose gel electrophoresis stained with ethidium bromide. Bands presenting the expected size, based on the cDNA sequence of the venom gland, were subcloned into plasmid vector pCRscript SK+ (Stratagene), by following manufacturer's instructions, and was submitted to sequencing by using oligonucleotides annealing in neighboring regions to the site of multiple cloning of the vector (primers T3 and T7).

C—Selection and Identification of Clones Codifying the Crotamine Precursor

Clones containing cDNA codifying the crotamine precursor were isolated by using a method based on PCR reactions with high stringency (Israel, D. I. (1993), *A PCR-Based Method for High Stringency Screening of DNA Libraries, Nucl. Ac. Res.* 21, 2627-2631). In this method, the phage library was subdivided into 64 aliquots of 1000 plaques in each well of a micro plate and then was submitted to amplification for six hours. The wells containing clones with insert codifying crotamine were identified by means of PCR reactions using specific oligonucleotides, allowing the amplification of a fragment of about 100 base pairs, which specificity was confirmed by hybridization reactions with specific probes. Phages of positive wells were then diluted and again aliquoted in wells containing 25 plaques each one, being again reamplified and submitted to a new step of selection by means of PCR reactions, as already described. After three selection cycles, all randomly collected plaques contained cDNA codifying crotamine precursor.

Alternatively, fragments obtained by PCR amplification from the total lysate of the cDNA library from the venom gland or by RT-PCR (reverse-transcriptase polymerase chain reaction), using specific oligonucleotides, were used for the synthesis of radioactive probes (marked with $\alpha$-$^{32}P$) by the random priming method (Rediprime kit/Amersham Biosciences). Nitrocellulose membranes (Schleicher & Schuell) prepared by using plates containing approximately 50 phage plaques each, were submitted to hybridization with radioactive probes in a 6×SSPE solution (1×SSPE: 0.15 M NaCl, 15 mM $NaH_2PO_4$, pH 7, 1 mM EDTA), 50% formamide, 0.1% SDS and 5×Denhardt's at 42° C. for 16 hours. Membranes were then washed twice in 2×SSC/0.1% SDS and three times in 0.1×SSC/0.1% SDS at 65° C. for 15 minutes each (1×SSC: 0.15 M NaCl and 15 mM sodium citrate, pH 7). Positive plaques for probes used were identified by auto-radiography and only plaques identified as positives were isolated for the analysis of the DNA insert. The analysis of identified inserts was made by sequencing the ends of the insert, soon after the in vivo excision of the pBluescript phagomide from the vector λ ZAP, which was made with the help of the helper phage, following manufacturer's instructions.

D—Sequencing of DNA Inserts

Sequencing reactions were made by following the chain termination method with dideoxy-nucleotides by using the Big Dye kit (Applied Biosystems), followed by the sequence analysis on the equipment ABI 310 or ABI 3100 (Applied Biosystem), following manufacturer's instructions.

Clone selection by hybridization of the cDNA library of a venom gland of *Crotalus durissus terrificus* allowed the isolation of the cDNA codifying the crotamine precursor. From the cDNA library of a pair of venom glands of a specimen of rattlesnake, 15 positive clones were isolated and sequenced. All sequenced cDNA clones, containing 340 to 360 nucleotide inserts, presented open reading frame of the same size (around 198 nucleotides). The alignment of said 15 sequences by using the MACAW software allowed to verify that these cDNAs could be joined into six different groups, by identifying six different cDNAs codifying two different isoforms of a crotamine precursor (FIG. 4). The crotamine precursor is constituted by 63 amino acid residues, wherein 22 amino acids on the N-terminal constitute a signal peptide, 42 amino acids correspond to the mature protein with a lysine at the C-terminal end which is removed after translation.

Example 4

Solid Phase Peptide Synthesis Processes

A—Use of the tert-Butyloxycarbonyl (Boc) Group as a Temporary Protector for the Amino Group and Benzyl (Bzl) Derivatives for the Protection of Most Reactive Side Chains of Amino Acids The first step of synthesis in this strategy is to remove the Boc group from the first amino acid residue linked to the resin.

Such removal occurs under the presence of 30% TFA in dichloromethane (DCM), containing 2% anisol, for 30 minutes. After this period, washes are made with isopropanol I/2% anisol, DCM and MeOH. To enter the next amino acid, the amino group is deprotonated (neutralized) with treatment under 10% TEA or 5% DIPEA in DCM for ten minutes. Subsequently, peptidyl resin is washed with DCM, MeOH, DCM and the solvent to be used in the coupling step.

Amino acid coupling passes through an activation step, which is usually made with coupling reagents: diisopropylcarbodiimide (DIC) or 2-(1H-benzotriazolyl-1,1,3,3-tetramethyluronium) tetrafluoroborate (TBTU). Three-time molar excess of Boc-amino acid (carboxylic component, CC) and the coupling agent over the content of amino groups (aminic component (CA)) is usually employed in the resin.

The proportion of reagents when DIC is used is: CA:CC:DIC, 1:3:3 and, when TBTU is used, the CA:CC:TBTU:DIEA ratio is now 1:3:3:4. The final concentration of these reagents is between 0.05 and 0.1 M.

While coupling Asn (asparagine) or Gln (glutamine), N-hydroxybenzotriazole (HOBt) is used together with the coupling compound, to avoid the formation of nitrile of these amino acids. In such couplings, the final proportion of CA:C-C:TBTU:HOBt:DIEA is 1:3:3:3:5. Monitoring of the coupling reaction, usually lasting two hours, is made by the qualitative ninhidrine method and blue color in peptidyl resin indicates incomplete coupling. In this case, recoupling is usually made by varying the solvent as used in the previous coupling and/or the coupling agent. After this coupling step is ended, the following cycle starts with the deprotection of the amino group up to the inlet of the subsequent residue and then cyclically up to the end of the elongation of the intended sequence.

After closing the synthesis, cleavage of the peptide from the resin and full deprotection of its side chains of amino acids are effected in one single treatment step with anhydrous HF at 0° C. for 60 minutes to 90 minutes in the presence of p-cresol and dimethyl sulfate (DMS) (5%, v/v of each one), which act as suppressants of side reactions induced by carbocations (carbonium ions) released during said HF treatment. In peptidic sequences containing Trp residues, ethane-1,2-dithiol (EDT) is added for the removal of the formyl group protecting the side chain of said amino acid to be made simultaneously to cleavage. EDT is used under the same proportion of the other suppressants (5% v/v from each one). After cleavage, the resin is washed with ethyl acetate and the peptide is extracted with 5% acetic acid washings (AcOH) in water (v/v), followed by lyophilization to finally obtain a white and usually amorphous powder.

B—Use of the Base-Labile Protectant 9-Fluorenylmethyloxycarbonyl (Fmoc) and Tert-Butyl Derivatives (TBU)

Differently from the previous strategy, the aminic protectant group Fmoc is removed from the amino acid with a treatment in 20% piperidine solution in DMF for about 20 minutes. This treatment already leaves amino groups in deprotonated form for the next coupling step. Coupling methods are the same of Boc chemistry and the final cleavage is made in acid medium which are weaker than HF, since both the linkage of the protection groups for the side chains (usually from the terc-butyl type) and the peptide to the resin is more labile than observed for Boc chemistry. 85% to 95% (v/v) TFA treatment is usually employed, plus a mixture of different kinds of supressants for side reactions for about two hours. After this step, the peptide precipitates in ice cold ethyl ether together with the resin and is centrifuged at 8000 rpm for five minutes. The supernatant is discarded and the residue is again suspended in ethyl ether, vortexed and centrifuged. This procedure is repeated about five times and, after such washings and precipitations, the resin and peptide mixture is dried under vacuum. The peptide is finally extracted from the resin with 5% AcOH (v/v) in water and the filtered is lyophilized until an amorphous white powder is obtained.

Both strategies A and B were previously disclosed by Barany, G. and Merrifield, R. B. (Gross, E., Meinhofer, J. (Eds.) (1980) in *The Peptides: Analysis, Synthesis and Biology*, vol. II, Academic Press, New York, U.S.A.; Fields, G. B., Noble, R. L. (1990), *Int. J. Pep. Prot. Res.* 35, 161).

Example 5

In Vitro Cell Culture and Cell Differentiation

Embrionary stem cells (ES) from mice, line USP-1 (Soukoyan, M. A., Kerkis, A. Y., Mello, M. R. B., Kerkis, I. E., Visintin, J. A., Pereira, L. V. (2002), *Establishment of New Murine Embryonic Stem Cell Lines for the Generation of Mouse Models of Human Genetic Diseases, Braz. J. Med. Biol. Res.* 35, 535-542) in the passage 8-10 were cultured on a layer of γ-irradiated embrionary fibroblasts of mice, kept in DMEM (Gibco, U.S.A.), supplemented with 15% FCS (Gibco, U.S.A.), 1 mM sodium piruvate, 1% non-essential amino acids, 0.1 mM β-mercaptoethanol and 1×103 U/ml murine Leukemia Inhibitor Factor (LIF) (ESGRO-LIF, Gibco). Human lymphoblastoids and primary fibroblasts were cultivated in DMEM and in RPMI, respectively, supplemented with 10% FCS with no antibiotics. Cultures were kept under humid atmosphere at 37° C. and 5% $CO_2$.

The hanging drop method was used, with some amendments, to induce the differentiation of ES cells from USP-1 line (Wobus, A. M., Wallukat, G., Hescheler, J. (1991), *Pluripotent Mouse Embryonic Cells are Able to Differentiate into Cardiomyocytes Expressing Chronotropic Responses to Adrenergic and Cholinergic Agents and $Ca^{2+}$ Channel Blockers, Differentiation* 48, 173-182). Briefly, ES cell suspensions without fibroblasts were obtained, collected with 0.25% trypsin/EDTA (Gibco, U.S.A.). Said suspension was diluted up to $3.5\times10^4$ cells/ml and dropped by using a micropipette (25 μl per drop) on the Petri dish cap (10 cm). Drops adhered to the surface were turned upside down over the plate already containing 5 ml PBS. After three days in a $CO_2$ oven, in the hanging drop culture in appropriate culture medium for ES, with no LIF, aggregates are formed, known as embryonic bodies (EBs). EBs were later transferred to another plate (35 mm) with a 1% agarose layer, and maintained in the $CO_2$ oven at 37° C. On the fifth day, EBs were transferred to microscope slides, on another Petri dish, where they adhered and started differentiating into a monolayer.

Standard histochemistry methods were used to detect the alkaline phosphatase activity on non-differentiated cells.

Example 6

Conjugation of Crotamine with Fluorescent Dye Agent Cy3

Crotamine (1 mg) was suspended in 1 ml buffer (100 mM sodium carbonate/bicarbonate, pH 9.3) and conjugated to the fluorescent dye Cy3, a cyanine derivative supplied as a bifunctional form of an NHS-type ester in the Fluorolink Cy3 dye pack kit (Amersham Biosciences). To verify if Cy3-crotamine is biologically active, a sublethal dose, 50 μg of the conjugate (corresponding to 2.5 mg of toxin/kg) was intraperitoneally injected into a mouse. The crotamine linked to Cy3 complex caused the typical paralysis response of the hind legs in less than 15 minutes after injection.

Example 7

Embriotoxicity Assay

Bearing in mind that crotamine is a toxin, cytotoxic effects were tested on embryonic stem cells (ES) of mice which are non-differentiated cells, derived from the embryonic bud of blastocytes, and have as their main characteristic their pluripotence, an ability to differentiate to different types of tissues.

Such cells were chosen bearing in mind the usefulness of crotamine application for gene therapy (by means of stem cells) and transgenesis, as a carrier of other molecules to within cells. Four different concentrations were tested for five days. Tests concluded that, under submicromolar concentrations, between $10^{-6}$ and $10^{-7}$ M, crotamine does not present any cytotoxic effect on embryonic stem cells in culture. The assay was as follows.

Embryonic bodies (EBs) were obtained by the hanging drop method, as described above, using culture medium containing crotamine at various concentrations (100 μM to 0.1 μM), changing the medium every two to three days. To analyze the crotamine location in EBs under development, crotamine was substituted with crotamine linked to Cy3 (Cy3-crotamine) during the final 24 hours of incubation. Compact murine morulae (8-16 cells) were obtained from the oviduct and cultivated for 24 hours at 37° C. in 5% $CO_2$, in individual microwells of V-bottom plates (Costar) with 98 microwells in M16 medium (supplier: Sigma) and Cy3-crotamine (1-0.1 μM). After 24 hours of culture, normally developed blastocyst numbers were compared within the control and the experimental group.

Example 8

Incorporation of Crotamine

In vitro assay: Semiconffluent cultures of pluripotent and differentiation ES cells (homogeneous cell population), as well as other cell cultures of normal and tumor origin, were kept in small laminar slides placed in 24-well plates containing appropriate culture medium. Cells were incubated for 2-3 minutes to 72 hours in the presence of Cy3-crotamine, under concentrations between 10 μM and 0.01 μM, or as control, just in the presence of the dye agent Cy3 diluted in 1 ml PBS (control). In in vivo assays, 1 ml of 1 μM Cy3-crotamine or the pure control dye agent Cy3 (1 ml) in PBS were intraperitoneally injected into a mouse (line CD-1). After 3 hours, cells from the bone marrow (mixed cell population), spleen and peritoneal liquid (mixed cell population) were isolated. Cells from the peritoneal liquid adhered to the microscope slides for one hour in RPMI medium supplemented with 10% FCS and no antibiotics at 37° C., under humid atmosphere and 5% $CO_2$. In all assays, cells were washed twice with cold solutions of 0.1 M PBS, pH 7.4, fixed with 3.7% formaldehyde in PBS for fifteen minutes and washed twice with PBS. Microscope slides were prepared in the PBS/glycerol (1:1) solution. Alternatively, non-fixed cells were washed twice with PBS and observed in the confocal microscope.

To analyze the specific binding of Cy3-crotamine to chromatin and centrosome (a pair of small organelles named the centrioles), the same experimental procedure, as described above, was used, the sole difference consisting in the pretreatment of ES cells and murine embryonic fibroblasts with 1 μM of free crotamine, followed by treatment with the conjugated crotamine, Cy3-crotamine, for 15 minutes more. A similar experiment was conducted in vivo, by injecting in mice both the conjugated and the free crotamine. As a control, 1 μM of Cy3-crotamine was used and incubated for 15 minutes. For the confocal microscopy analysis, cells were prepared as described above. Experiments with animals were carried out according to the international ethical recommendations for the use of animals.

Example 9

Chromosome Analysis

1 μM crotamine conjugated to Cy3 was added to the culture of ES-USP1 cells, human lymphoblastoids and primary fibroblasts for 1, 3, 6 and 24 hours. Cells were collected and treated according to the routine cytogenetic protocol, with no addition of colchicine. Digital images were obtained with refrigerated CCD (PCO, VC44) and processed by using ISIS software (MetaSystem).

We verified that crotamine binds to chromosomes in the metaphase, by comparing cells dyed with DAPI or 5-BrDU. Apparently, crotamine binds to the chromosome on phase S/G2 and on phase G2/M, during the condensation of the chromosome, when fluorescent markers become evident in all chromosomes. At the end of telophase, it is observed that crotamine remains restricted only to cytoplasm and 16 to 24 hours after the removal of crotamine from the culture medium, crotamine is no longer detected inside the cells, which makes it different from VP22 derived from herpes simplex, which also binds to chromatin after the internalization and it is secreted to daughter cells (Martin, A., O'Hare, P., McLauchlan, J., Elliott, G. (2002), *Herpes Simplex's Virus Tegument Protein VP22 Contains Overlapping Domains for Cytoplasmic Localization, Microtubule Interaction and Chromatin Binding, J. Virol.* 76, 4961-4970).

Example 10

Marker for Actively Proliferating Cells and Centrosome

Embryonic bodies, obtained according to the protocol as described above, after three days, adhered to small glass slides. On the following day, actively proliferating cells were simultaneously labeled with 5-bromo-2'-deoxyuridine (BrDU) and Cy3-crotamine. BrDU-labeled cell detection by the monoclonal antibody anti-BrDU (clone BU-1) was made according to manufacturer's recommendations (Amersham-Pharmacia Biotech). The secondary antibody was conjugated to the fluorescent compound FITC. BrDU and Cy3-crotamine were simultaneously added to the culture medium and, after three hours, cells were washed twice with cold 0.1 M PBS, pH 7.4. Cells were then fixed with 3.7% formaldehyde in PBS for 15 minutes and washed twice with PBS. Microscope slides were assembled in a PBS/glycerol solution (1:1) and analysed in a confocal microscope. To analyse colocalization of crotamine with centrioles in ES cells, the monoclonal antibody anti-tubulin, specific for cytoplasma and mitotic microtubules, was used.

We verified that Cy3-crotamine functions as a marker for the centrosome cycle. Strong marking of the centrosome in cells from the peritoneal liquid of mice in different steps of the cell cycle may be observed on FIG. 9. To analyse the association between crotamine and centrioles on ES cells, anti-tubulin a antibodies were used to highlight microtubules from the mitotic fuse, mitotic poles and centrioles (FIG. 9B). Cy3-crotamine is co-localized with mitotic poles, suggesting its association with centrosome (FIG. 9C). Furthermore, chromatin is linked to chromosomes anchored to the mitotic fuse as recognized by the anti-tubulin antibody (FIG. 9C). The process of duplication and separation of the centrosome was observed in cells from the peritoneal liquid treated with Cy3-crotamine (FIGS. 9D-R). Initially, pericentriole material linked to a pair of centrioles in G1 phase was strongly marked by Cy3-crotamine (FIGS. 9D, I, N). Fluorescence was observed in the nuclei of cells in S/G2 stage, when centrioles start to separate, and where chromosomal segregation is observed (FIGS. 9-E, J, O). Two centrioles migrating to opposed poles during prophase (FIG. 9-F, K, P), confirming clear association between crotamine and the chromosome. During metaphase (FIG. 9—G, L, Q) and anaphase (FIG. 9—H, M, R), an intense fluorescence observed on the chromosome and in centrioles located in opposed poles.

Example 11

DNA-Peptide Complexes Formation

DNA-peptide complexes were prepared by following the protocol described for synthetic cell-penetrating peptides: 50 μg DNA were added to 500 μl Hepes-buffered mannitol (HBM) buffer (0.27 M mannitol, 5 mM Hepes, pH 7.5) with 5-75 mmol of peptide in 500 μl HBM. Later on, the mixture was vortexed (5 min) to produce different complexes in load ratio ($NH^+_4$:$PO^-_4$), calculated between 0.1 and 2.4.

The interaction between crotamine and DNA was analysed by an interference assay for DNA migration in agarose gel. 1 μg DNA and an increasing concentration of crotamine was added in a total volume of 25 μl, containing 150 mM NaCl. Twenty minutes after the mixture was prepared, samples were analysed by agarose gel electrophoresis (1%), using Trisborate-EDTA buffer, followed by visualization by staining the nucleic acid with the ethidium bromide.

We verified that chromatin interaction with DNA, using various molar proportions of crotamine and linear and/or circular double strand DNA, and the formation of this complex interfere in the electrophoretic mobility of these compounds in agarose gel (FIG. 6). Electrophoresis in this system allows to observe alterations in the migration pattern (delay or shift in migration) due to the neutralization of the nucleic acid, caused by the presence of cationic peptide and/or due to the formation of larger complexes between crotamine and DNA.

Example 12

In Vitro and In Vivo Transfection

3T3 cells (spontaneously immortalized primary mouse fibroblasts) or COS-7 (cells derived from kidney of African green monkey) were plated ($1.5\times10^5$) in 6-wells plate (dimension of 6×35 mm), containing DMEM culture medium with 10% fetal bovine serum (FBS) and 200 mM L-glutamine, with no antibiotics, 1 or 2 days before the transfection until reaching 60% to 80% confluence of the plate. Transfection was performed in DMEM medium (2% ml/35 mm well) with 2% FBS and 80 or 100 μM chloroquine. Aggregates (crotamine plus 2 μg DNA in 0.2 ml HBM) were added in each well, on the cells in culture. After five hours of incubation at 37° C., under humid atmosphere and 5% $CO_2$, the medium was substituted with another one containing 10% FBS. In the control culture wells, DNA was added in the same concentration and they were processed in the same way of experimental samples. After 24 and 48 hours, cells were washed with PBSA and fixed with 3.7% formaldehyde. The transfection medium was substituted with DMEM medium, containing 10% FBS, and the transgenic expression was then evaluated 24 to 48 hours after the transfection. The efficiency of transfection as determined by DNA-peptide aggregates was compared with that obtained by using lipofectamine, following routine protocol.

Transfection was also carried out in the presence of dimethylamyloride (final concentration 62.5-250 μM) and cytochalasin b (final concentration 5-40 μM) as disclosed above, except that the drug was added to the cells kept in medium with no serum, before the addition of aggregates (10 and 30 minutes before transfection, respectively). For transfections with methyl-β-cyclodextrin (MβCD) or methyl-β-cyclodextrin with cholesterol (MβCD-col; final concentration 5-10 mM), cells were incubated for one hour with the drug in medium with no serum before transfection.

For in vivo transfection, DNA-peptide aggregate was prepared by replacing HBM buffer by PBSA pH 7.5. This mixture was then intraperitoneally injected in a mouse, and the tissues were analysed for the presence of the transgene after 24 and 48 hours.

We verified that, in vitro, human fibroblasts were intensively marked after one hour of incubation with crotamine (FIG. 2A), showing strong fluorescence on round cells, supposedly in a cell division process (FIGS. 2B and C) and weak signal on quiescent ones. Murine pluripotent embryonic stem cells presented strong signal on cell islets, composed by round and juxtapositioned cells grown over an irradiated mouse fibroblast layer (FIGS. 2D and E), in contrast to a weak background signal as observed for the culture of control ES cells after 3-hour treatment with the fluorescent dye agent Cy3 (FIG. 2F). In vitro transfection, which showed positive results, was also carried out with human limfoblastoids, B16 murine melanoma cells, HCT116 colon cancer cells, human mesenchymal stem cells from bone marrow and dental pulp and all under appropriate cell culture conditions.

Figure 1:
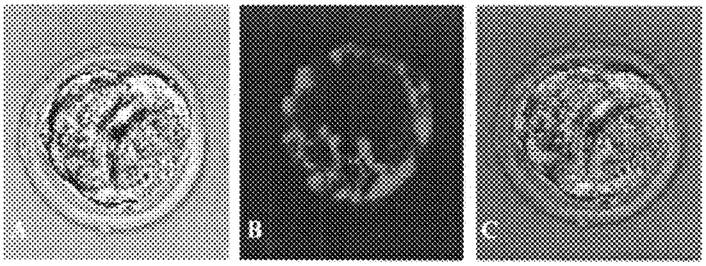
FIG. 1 shows the internalization of Cy3-conjugated crotamine in blastocyts in vitro, wherein the (A) digital interference contrasts, (B) the fluorescence as observed by confocal microscopy and (C) the overlaying of images obtained in (A) and (B) are presented, showing a intense fluorescence in the cell cytoplasm.
Figure 2:
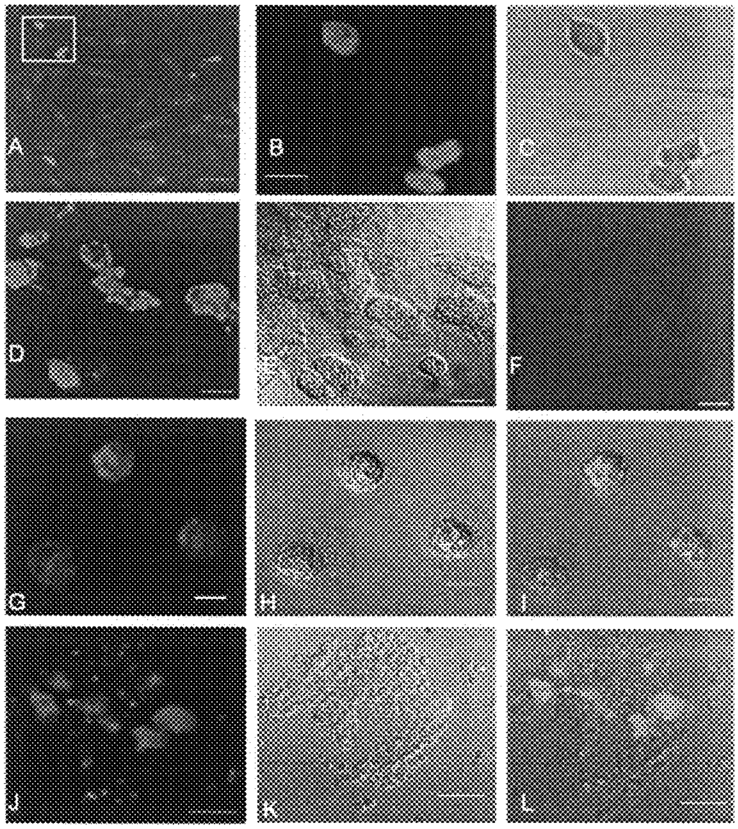
FIG. 2 shows in vitro internalization and localization of Cy3-crotamine (1 μM) in different cells types. (A-C) show in vitro internalization in human fibroblasts after one hour of treatment; (D and E) show in vitro internalization in stem cells after one hour of treatment; (F) shows the culture of control ES cells (embryonic stem) after treatment for three hours, only with the fluorescent Cy3 dye; (G-I) show in vitro internalization in peritoneal liquid cells; (J-L) show the marks observed in murine bone marrow cells isolated after Cy3-crotamine injection in mice.
Figure 3:
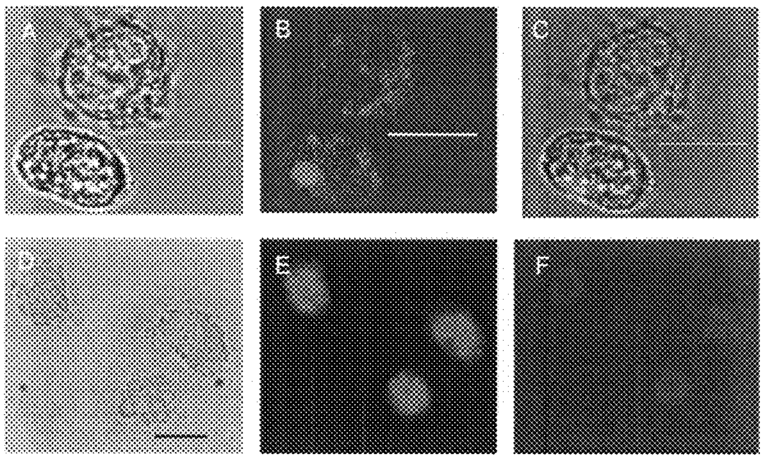
FIG. 3 shows the internalization of Cy3-conjugated crotamine in living cells. (A-C) show living cells of the peritoneal liquid of mice, presenting strong and moderate signals in cytoplasm and nucleus, respectively; (D-F) show living cells of the peritoneal liquid of mice, showing the nuclear localization of crotamine.
Figure 5:
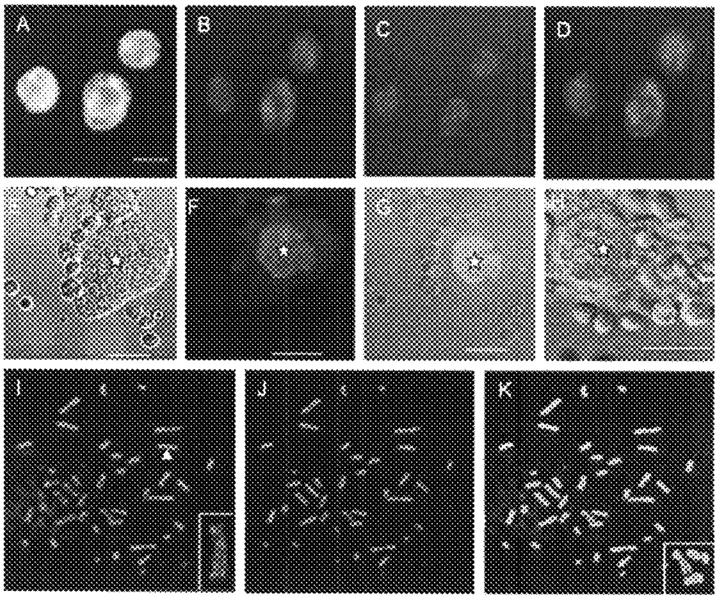
FIG. 5 shows the intracellular localization and the binding of Cy3-crotamine to chromosomes in mitosis, as observed in vitro and in vivo.

We verified that, in vivo, three hours after the intraperitoneal injection of Cy3-crotamine in CD-1 strain mice, strong signals were observed on the cytoplasm and nucleus of the cells from the peritoneal liquid (FIG. 2—G, H, I) and cells from the murine bone marrow (FIG. 2—J, K, L). In controls, where only the fluorescent dye agent Cy3 was injected, only a weak background signal can be observed.

Example 13

Determination of Interaction Between Crotamine and DNA

A—Analysis of the DNA-Peptide Interaction by Agarose Gel Electrophoresis (Gel Shift Assay)

The formation of the complex between the peptide and DNA was analysed by the electrophoretic mobility of the complex in agarose gel (1%, w/v) by varying the molar proportions between the peptide and the double-strand DNA. Tests were made by mixing plasmid DNA (2 or 4 μg) with 10 μg of pure crotamine, in the presence or absence of 150 mM NaCl, which were applied on agarose gel immersed in Tris borate-EDTA buffer. DNA was then observed after staining with ethidium bromide and using UV light transiluminator. Gel documentation after electrophoresis was made by using an image digitizer (model FLA3000). This system of electrophoresis allows to observe changes in the migration pattern (migration delay) due to the neutralization of nucleic acid by cationic peptide present and/or due to the formation of larger complexes between crotamine and DNA (FIG. 6). Table 1 indicates the composition of the mixtures prepared with the DNA+crotamine applied to the agarose gel.

TABLE 1

Composition of the mixtures prepared with the DNA + crotamine

| | 1 | 2 | 3 | 4 | 5 | 6 | 7 | 8 | 9 | 10 | 11 | 12 |
|---|---|---|---|---|---|---|---|---|---|---|---|---|
| Circular DNA | 2 μg | 2 μg | 2 μg | 4 μg | 4 μg | 4 μg | — | — | — | — | — | — |
| Linear DNA | — | — | — | — | — | — | 2 μg | 2 μg | 2 μg | 4 μg | 4 μg | 4 μg |
| Cy3-crotamine | 10 μg | — | — | 10 μg | — | — | 10 μg | — | — | 10 μg | — | — |
| crotamine | — | 10 μg | — | — | 10 μg | — | — | 10 μg | — | — | 10 μg | — |

B—Analysis of the Peptide-DNA Interaction by Circular Dichroism

Circular dichroism spectra were taken in a spectropolarymeter JASCO 810 with a Peltier system for temperature control. The device is regularly calibrated with recrystallized d-10 camphorsulfonic acid. Standards used for the equipment were: wavelength range 190-260 nm; sensitivity 100 mdeg; resolution 0.5 nm; response 8 s; reading speed 50 nm/min; 8 accumulations; temperature 37° C. Samples were analysed in a 1 mm optical path cell in 10 mM sodium phosphate buffer, pH 7.4, in the presence or absence of 150 mM NaCl. The crotamine concentration used was 20 μM and plasmid DNA concentration was 0.1 μM. CD spectra for crotamine and the circular DNA sample (plasmid) were separately collected and mixed in a molar ratio of 200:1 (crotamine:DNA) as described above.

We verified that obtained spectra for the mixed compounds under the above described proportion and the stoichiometric proportion (1:1) presented differences when compared with the theoretical spectrum as obtained by adding spectra individually obtained for crotamine and the DNA sample, indicating the presence of interaction between crotamine and the plasmid DNA causing a conformational change. Such interaction may be verified in the experiments made, both in the absence and in the presence of 150 mM NaCl, and it could be better seen under the molar ratio 200:1 (crotamine:DNA), due to the large difference in molecular weight of these two molecules (FIG. 7).

Example 14

Peptide Fragments Derived from Crotamine

Two peptides were synthesized based on crotamine sequence, e.g. two sequences corresponding to fragments of crotamine, i.e. Crot2-18 (KQCHKKGGHCFPKEKIC (SEQ ID NO: 3)), herewithin designated as peptide 1, and Crot27-39 (KMDCRWRWKCCKK (SEQ ID NO: 4)), herewithin designated as peptide 2. The ability and efficiency of these two peptides to transfect cells in vitro and in vivo were analysed. The same protocol which was used for natural crotamine, as described in Example 9 was followed: Peptides were mixed with the plasmid DNA containing the gene coding for GFP (green fluorescent protein). After forming the complex with DNA, peptides were put on Petri dishes containing 3T3 cell line and left in the $CO_2$ oven for 24 and 48 hours. Subsequently, cells were fixed and the result of transfection was analysed by confocal microscopy. As controls, the same cells were transfected by using Lipofectamin, as well as the crotamine molecule with 42 amino acid residues.

After the treatment, we observed a more intense green fluorescence corresponding to the stronger GFP expression when peptide 1 was used, in comparison with peptide 2. In both cases, the best result was obtained after 48 hours of treatment. Apparently, no distinctive signals were observed on 3T3 cells from actively proliferating cells, when compared with the original crotamine. Such results allow the use of the crotamine peptide fragments in gene therapy, mainly in cases involving tissues with low number of actively proliferating cells.

From the knowledge disclosed herein in the text, examples or figures, a skilled man in the art will know how to promptly put into practice numerous aspects of the present invention, not necessarily disclosed herewithin, but covered by the claims that follow.

Example 15

Mice Melanoma B16F10 Cell Line Culture

The cells were maintained in Dulbecco's modified Eagle's cell culture medium (DMEM; Invitrogen, Carlsbad, Calif.) supplemented with 15% fetal calf serum (FCS; Invitrogen). The cells were kept at 37° C. with humidity and 5% $CO_2$. After preparing a cell suspension with about $5\times10^6$ cells/ml of PBS [phosphate buffered solution], approximately 0.2 ml of this suspension was subcutaneously or endovenously (retro-orbital injection) injected into each Balb/c mouse, of 4 to 6 weeks-old with body weight between 16 to 20 g. For negative control, the animals were injected with 0.2 ml of PBS. Before setting up the experiments, the animals were kept under 12 hour light-dark cycle, and were allowed to have water and food ad libitum. All animals were caged and handled under ethical conditions according to international rules of animal care, stated by the International Animal Welfare Recommendations, and in accordance with the Guidelines for the Use of Animals in Biochemical Research Tumor labeling by cy3-crotamine:

Subcutaneous injection of B16F10 (n=6)

About 8 to 12 days after subcutaneous injection of B16F10 cells, the visible 'melanoma' tumors were removed and analyzed.

To observe the accumulation of fluorescently labeled crotamine [Cy3-crotamine] into tumors, injected mice were treated by a single intraperitoneal injection of 5 μg of cy3-crotamine/animal. 24 hours after, the animals were sacrificed and the 'melanoma' tumors and internal tissues were removed and analyzed [frozen/Tissue-Tek and Paraplast block preparations]. The frozen slices were stained with DAPI and analyzed by confocal microscopy. A strong fluorescent signal was observed inside the cell mass of B16F10 cells tumor. The cy3-crotamine was observed in the nucleus of the cells showing an overlay with the DAPI staining.

The tissue slices fixed in Paraplast were stained with hematoxilin and eosin, and were observed under light microscopy showing tumoral cells in the tumors and also in metastasis.

Endovenous injection of B16F10 (n=6)

After endovenous injection of B16F10 cells, the mice were observed during 21 days, and metastasis in the lung and liver were observed.

To observe the accumulation of fluorescently labeled crotamine [Cy3-crotamine] into tumors, injected mice were treated by a single intraperitoneal injection of 5 μg of cy3-crotamine/animal. 24 hours after, the animals were sacrificed and the internal tissues (including those showing metastasis) were removed and analyzed [frozen/Tissue-Tek and Paraplast block preparations]. The frozen slices were stained with DAPI and analyzed by confocal microscopy. A strong fluorescent signal was observed inside the cell mass of B16F10 cells tumor.

The tissue slices fixed in Paraplast were stained with hematoxilin and eosin, and were observed under light microscopy showing highly proliferative tumoral cells agromerates close to the tumors in the lung.

Control group (n=6)

The animals of the control group were injected with PBS and 21 days after they were treated with 5 μg of cy3-crotamine/animal by intravenous injection.

Tumor Treatment with Natural Crotamine:

30 minutes after endogenous injection of B16F10 cells, as described above, the animals were treated with 1 μg of crotamine/animal by daily subcutaneous injection, during 21 days. The animals were observed for about 50 days.

The daily treatment with crotamine determined a delay or even inhibited the tumor formation when compared to the control group animals:

| | $10^{th}$ | $11^{th}$ | $12^{th}$ | $13^{th}$ | $14^{th}$ | $15^{th}$ | $16^{th}$ | $17^{th}$ | $18^{th}$ | $19^{th}$ | $20^{th}$ | $21^{th}$ | Total |
|---|---|---|---|---|---|---|---|---|---|---|---|---|---|
| B16F10 | | 1 | | | | | 4 | 4 | | | 1 | | 10 posit. |
| Treated w/ crotamine | | | | | | | | | 3 | | 2 | | 5 posit. |

which means for:
B16F10=10 positives (58.8%) and 7 negatives (41.7%)=ratio 0.58
treated=5 positives (33.3%) and 10 negatives (66.6%)=ratio 0.33

After the $21^{st}$ day, the animals were further observed for 26 days:

| | $25^{th}$ | $29^{th}$ | $35^{th}$ | $48^{th}$ |
|---|---|---|---|---|
| B16F10 | 9 | 9 | 14 | 15 |
| Treated w/ crotamine | 9 | 9 | 12 | 12 |

which means for
B16F10=15 positives (88.2%) and 2 negatives (11.7%)
treated=12 positives (80%) and 3 negatives (20%)

Histological Analysis of Frozen Cuts:

Subcutaneous melanomas and internal organs with metastasis were fixed in PBS containing formaline 4%, the material was washed in PBS for 1 hour, the tissues were conserved with washes of saccharose 30, 50 and 75% PBS and included in Tissue-Tek (Sakura Finetechnical Co., Ltd., Tokyo, 103, Japan) overnight and frozen at −20° C. Cuts of 6 nm were carried out in a Kriostate microtome at −20° C.

Histological Analysis in Paraplast Blocks:

Subcutaneous melanomas and internal organs were fixed and washed in the same above-mentioned conditions and dehydrated with ethanol 30, 50, 75, 90 and 95% and bleached with xilol for 30 minutes. They were included in Paraplast with two baths of 30 minutes and blocked. The cuts of 6 nm were fixed at 70° C. and colored with hematoxilin-eosin (H.E.).

The invention claimed is:

1. A composition comprising a conjugate of crotamine consisting of SEQ ID No. 1 and a pharmaceutically effective compound for treating cancer, wherein:

(i) $aa^{1-3}$ of SEQ ID No. 1 are selected from the group consisting of basic amino acid residues and non-carried polar amino acid residues;

(ii) $aa^{5-10}$ of SEQ ID No. 1 are selected from the group consisting of basic amino acid residues and non-polar amino acid residues;

(iii) $aa^{12-17}$ of SEQ ID No. 1 are selected from the group consisting of basic amino acid residues, acid amino acid residues and non-polar amino acid residues;

(iv) $aa^{19-29}$ of SEQ ID No. 1 are selected from the group consisting of basic amino acid residues, acid amino acid residues, non-carried polar amino acid residues and non-polar amino acid residues;

(v) $aa^{31-35}$ of SEQ ID No. 1 are selected from the group consisting of basic amino acid residues and non-polar amino acid residues; and (vi) $aa^{38-42}$ of SEQ ID No. 1 are selected from the group consisting of basic amino acid residues, non-carried polar amino acid residues and non-polar amino acid residues, wherein the crotamine is present in an amount of 100 μM to 0.1 μM effective for the delivery of the pharmaceutically effective compound into cells.

2. The composition according to claim 1, wherein crotamine is present in an amount of about 1 μM to about 0.1 μM.

3. The composition according to claim 1, wherein crotamine further provides selectivity over actively proliferating cells.

4. The composition according to claim 1, wherein it is a pharmaceutical composition used for the treatment of dysfunctions, deficiencies and/or diseases related to cell proliferation.

5. The composition according to claim 1 for identifying or labeling cells amongst a homogeneous and/or a mixed cell population.

6. The composition according to claim 1, wherein:

(a) said basic amino acid residues are selected from the group consisting of: Lys, His, and Arg;

(b) said non-carried polar amino acid residues are selected from the group consisting of Gln, Ser, and Tyr;

(c) said non-polar amino acid residues are selected from the group consisting of Gly, Ile, Leu, Met, Phe, Pro, Trp; and (d) said acid amino acid residues are selected from the group consisting of Asp, and Glu.

7. The composition according to claim 6, wherein:

(a) said basic amino acid residues and said non-carried polar amino acid residues in $aa^{1-3}$ of SEQ ID No. 1 are Tyr, Lys, and Gln;

(b) said basic amino acid residues and said non-polar amino acid residues in $aa^{5-10}$ of SEQ ID No. 1 are His, Lys, Lys, Gly, Gly, His;

(c) said basic amino acid residues, acid amino acid residues and said non-polar amino acid residues in $aa^{12-17}$ of SEQ ID No. 1 are Phe, Pro, Lys, Glu, Lys, Ile;

(d) said basic amino acid residues, acid amino acid residues, non-carried polar amino acid residues and said non-polar amino acid residues in $aa^{19-29}$ of SEQ ID No. 1 are Leu, Pro, Pro, Ser, Ser, Asp, Phe, Gly, Lys, Met, Asp;

(e) said basic amino acid residues and said non-polar amino acid residues in $aa^{31-35}$ of SEQ ID No. 1 are Arg, Trp, Arg, Trp, Lys; and (f) said basic amino acid residues, non-carried polar amino acid residues and said non-polar amino acid residues in $aa^{38-42}$ of SEQ ID No. 1 are Lys, Lys, Gly, Ser, and Gly.

8. The composition according to claim 7 wherein the amino acid sequence of said SEQ ID No. 1 consists of SEQ ID No. 2.

* * * * *